United States Patent
Hawi

(10) Patent No.: US 9,624,233 B2
(45) Date of Patent: Apr. 18, 2017

(54) COMPOUNDS FOR TREATING PRURITIC CONDITIONS

(71) Applicant: TREVI THERAPEUTICS, INC., New Haven, CT (US)

(72) Inventor: Amale Hawi, Ridgefield, CT (US)

(73) Assignee: Trevi Therapeutics, Inc., New Haven, CT (US)

( * ) Notice: Subject to any disclaimer, the term of this patent is extended or adjusted under 35 U.S.C. 154(b) by 0 days.

(21) Appl. No.: 15/136,742

(22) Filed: Apr. 22, 2016

(65) Prior Publication Data

US 2016/0311832 A1 Oct. 27, 2016

Related U.S. Application Data

(60) Provisional application No. 62/151,618, filed on Apr. 23, 2015.

(51) Int. Cl.
*C07D 489/08* (2006.01)
*A61K 31/439* (2006.01)

(52) U.S. Cl.
CPC .................................. *C07D 489/08* (2013.01)

(58) Field of Classification Search
CPC .................................................... C07D 489/08
See application file for complete search history.

(56) References Cited

U.S. PATENT DOCUMENTS

| | | | |
|---|---|---|---|
| 4,477,456 A | 10/1984 | Ciganek | |
| 7,195,882 B2 * | 3/2007 | Root | C07D 498/12 |
| | | | 435/7.93 |
| 2011/0190331 A1 | 8/2011 | Avey et al. | |

FOREIGN PATENT DOCUMENTS

EP 0070427 A2 1/1983

OTHER PUBLICATIONS

International Search Report and Written Opinion for International Application No. PCT/US2016/029024, mailed Jul. 25, 2016, 7 pages.

* cited by examiner

*Primary Examiner* — Samantha Shterengarts
(74) *Attorney, Agent, or Firm* — Cooley LLP

(57) ABSTRACT

The present invention includes compounds having structural formula (I), or pharmaceutically acceptable salts, solvates, and/or esters thereof. These compounds are useful for treating itch or a pruritic condition. The present invention also includes compositions comprising the present compounds and methods of treating a pruritic condition. Furthermore, the present invention provides methods for preparing the compounds.

26 Claims, 14 Drawing Sheets

COMPOUNDS FOR TREATING PRURITIC CONDITIONS

CROSS-REFERENCE TO RELATED APPLICATIONS

The present application claims the benefit of priority to U.S. Provisional Application No. 62/151,618, filed on Apr. 23, 2015, the contents of which are hereby incorporated by reference in their entirety.

FIELD OF THE INVENTION

The invention relates to compounds, compositions, and methods useful for treating pruritic conditions.

BACKGROUND OF THE INVENTION

Pruritus, or itch, is a sensation that stimulates the desire or reflex to scratch, which can be either generalized or localized. The cause of pruritus is not fully understood. Proposed contributors to the pathogenesis of pruritus may include anemia or other manifestation of erythropoietin deficiency, histamine release from skin mast cells, skin dryness, secondary hyperparathyroidism, hyperphosphatemia with increased calcium phosphate deposition in the skin and alterations in the endogenous opioidergic system with overexpression of opioid receptors.

The present invention provides compounds, compositions, and methods useful for treating pruritus or itch.

SUMMARY OF THE INVENTION

In one embodiment, the present invention provides a compound having structural formula (I):

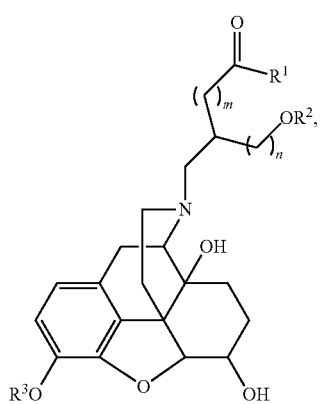

(I)

or a salt, solvate or ester thereof, wherein:

$R^1$ is alkyl, $OR^4$, or $NR^5R^6$;

$R^2$ is H or alkyl; or alternatively, le and $OR^2$, together with the atoms to which they are attached, form a lactone ring;

m is 0 or 1;

n is 1 or 2; and $R^3$, $R^4$, $R^5$ and $R^6$ are independently hydrogen or alkyl.

In another embodiment, the present invention provides a compound having structural formula (II):

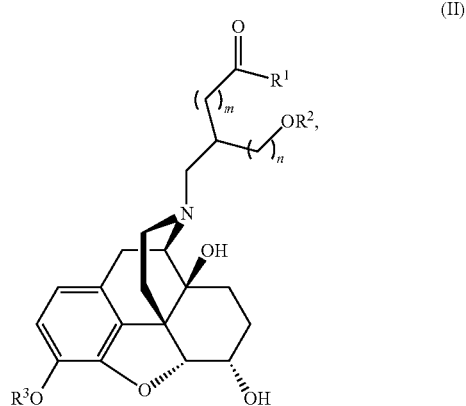

(II)

or a salt, solvate, or ester thereof, wherein $R^1$, $R^2$, $R^3$, $R^4$, $R^5$ and $R^6$ and m and n are as defined above.

In another embodiment, the present invention provides pharmaceutical compositions comprising a compound of formula (I) or (II), or a salt, solvate, or ester thereof; and a pharmaceutically acceptable excipient.

In another embodiment, the present invention provides a unit dosage form comprising a compound of formula (I) or (II), or a salt, solvate, or ester thereof and a pharmaceutically acceptable excipient. In some embodiments, the unit dosage form is an extended release (ER) dosage form.

In another embodiment, the present invention provides a method for treating a pruritic condition comprising administering an effective amount of a compound of formula (I) or (II), or a salt, solvate, or ester thereof, to a subject in need thereof.

In another embodiment, the present invention provides methods for preparing a compound of the present invention.

DETAILED DESCRIPTION OF THE INVENTION

Figure 1:
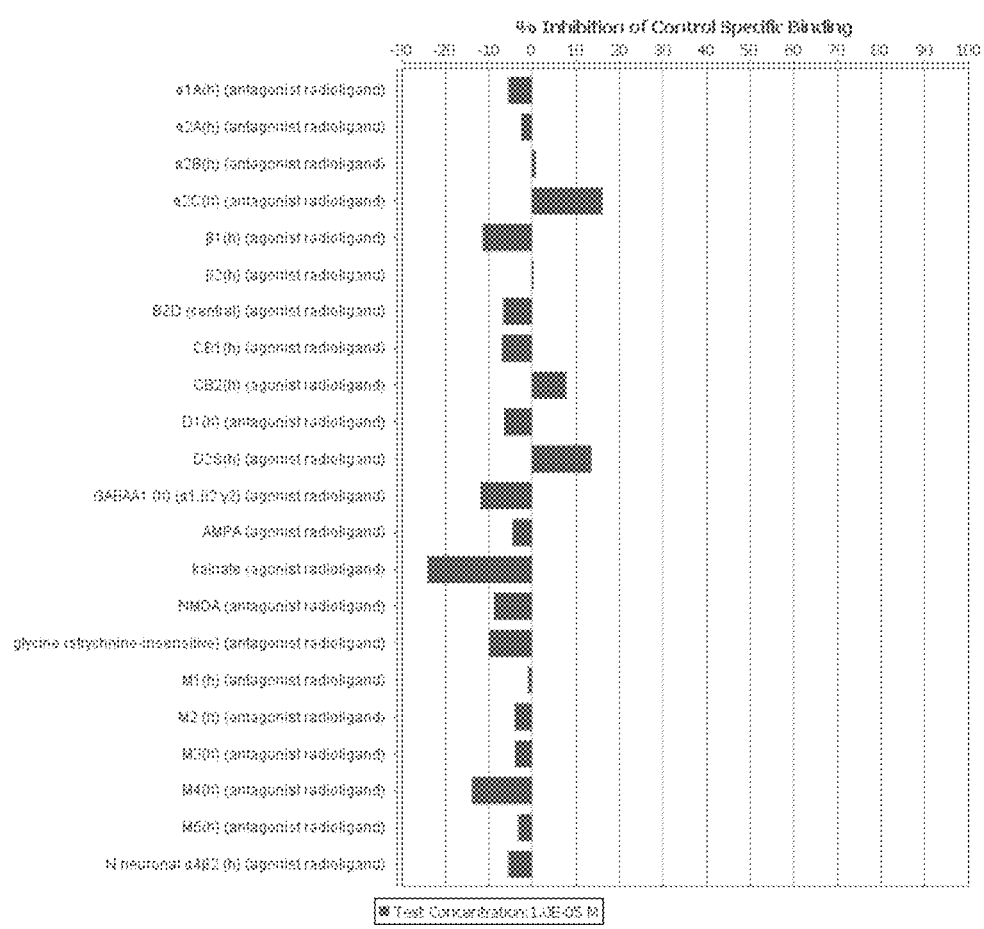
FIG. 1 is a histogram showing the results of an in vitro binding affinity screen performed on the first set of 22 targets to assess the abuse potential of nalbuphine.
Figure 2:
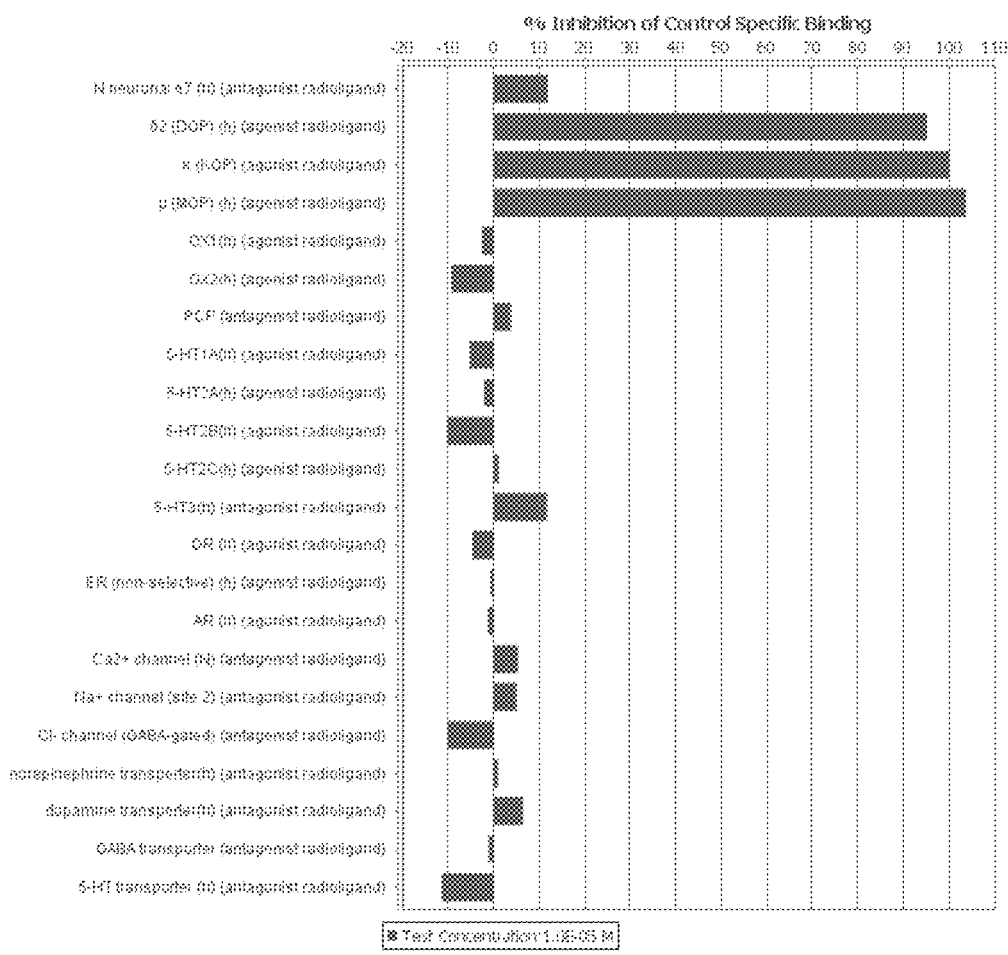
FIG. 2 is a histogram showing the results of an in vitro binding affinity screen performed on the second set of 22 targets to assess the abuse potential of nalbuphine.
Figure 3:
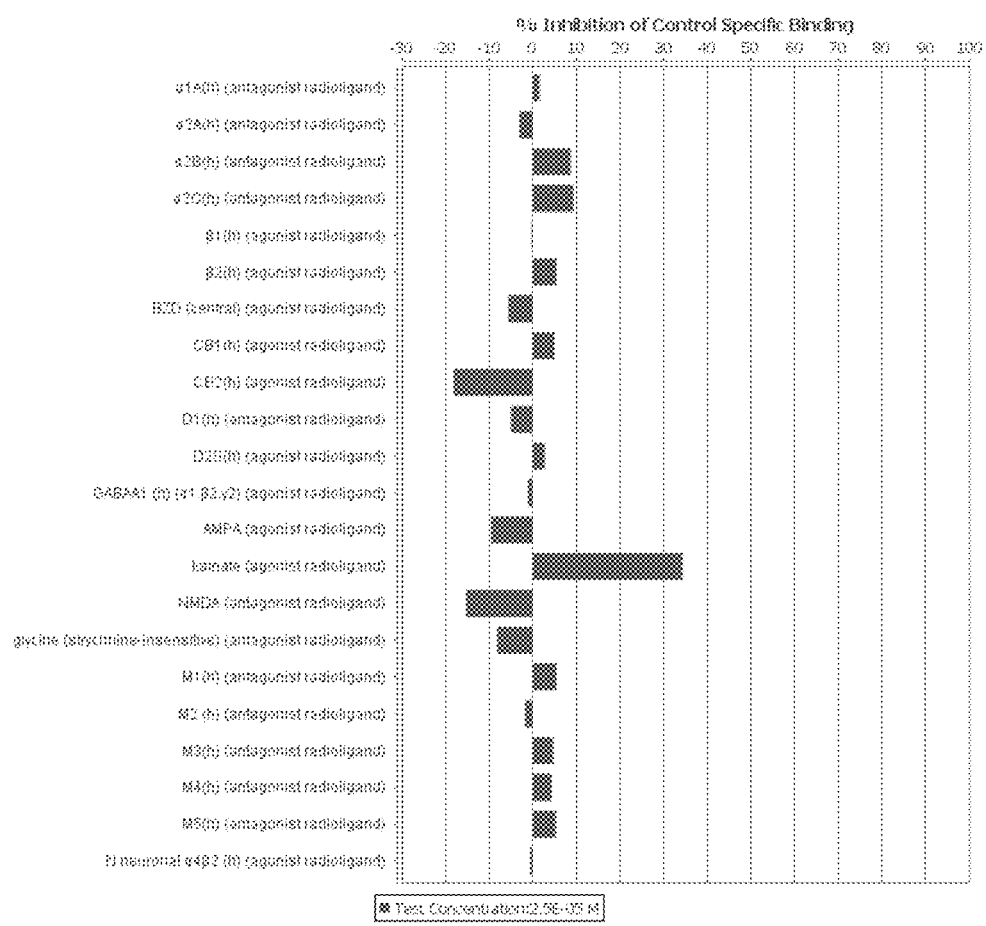
FIG. 3 is a histogram showing the results of an in vitro binding affinity screen performed on the first set of 22 targets to assess the abuse potential of nalbuphine-3-beta-D-glucuronid.
Figure 4:
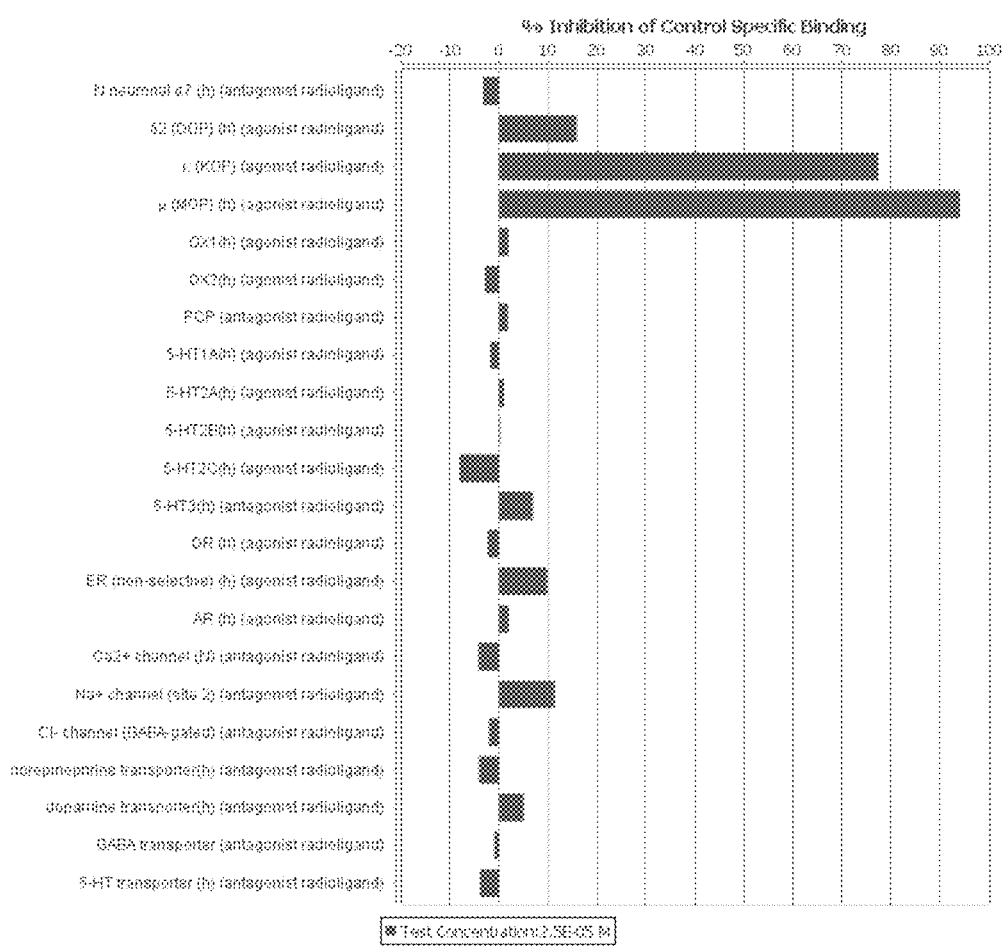
FIG. 4 is a histogram showing the results of an in vitro binding affinity screen performed on the second set of 22 targets to assess the abuse potential of nalbuphine-3-beta-D-glucuronid.
Figure 5:
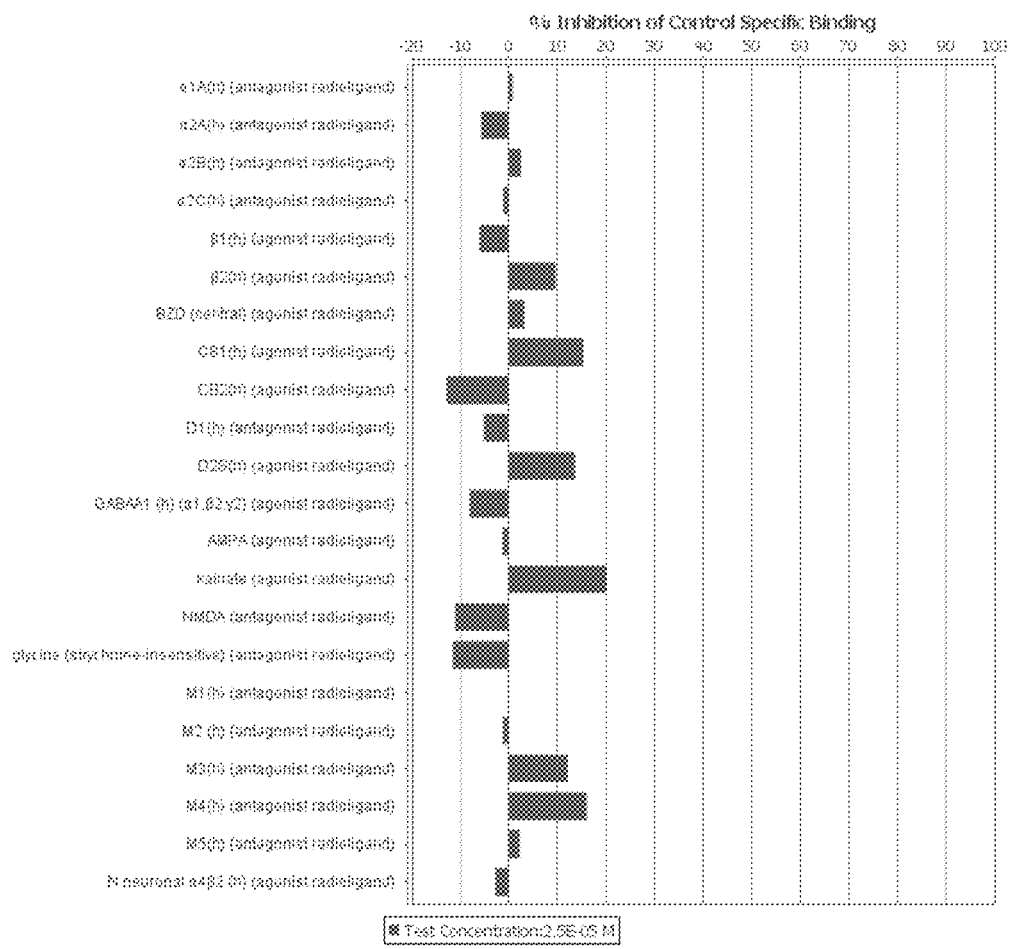
FIG. 5 is a histogram showing the results of an in vitro binding affinity screen performed on the first set of 22 targets to assess the abuse potential of Compound 1.
Figure 6:
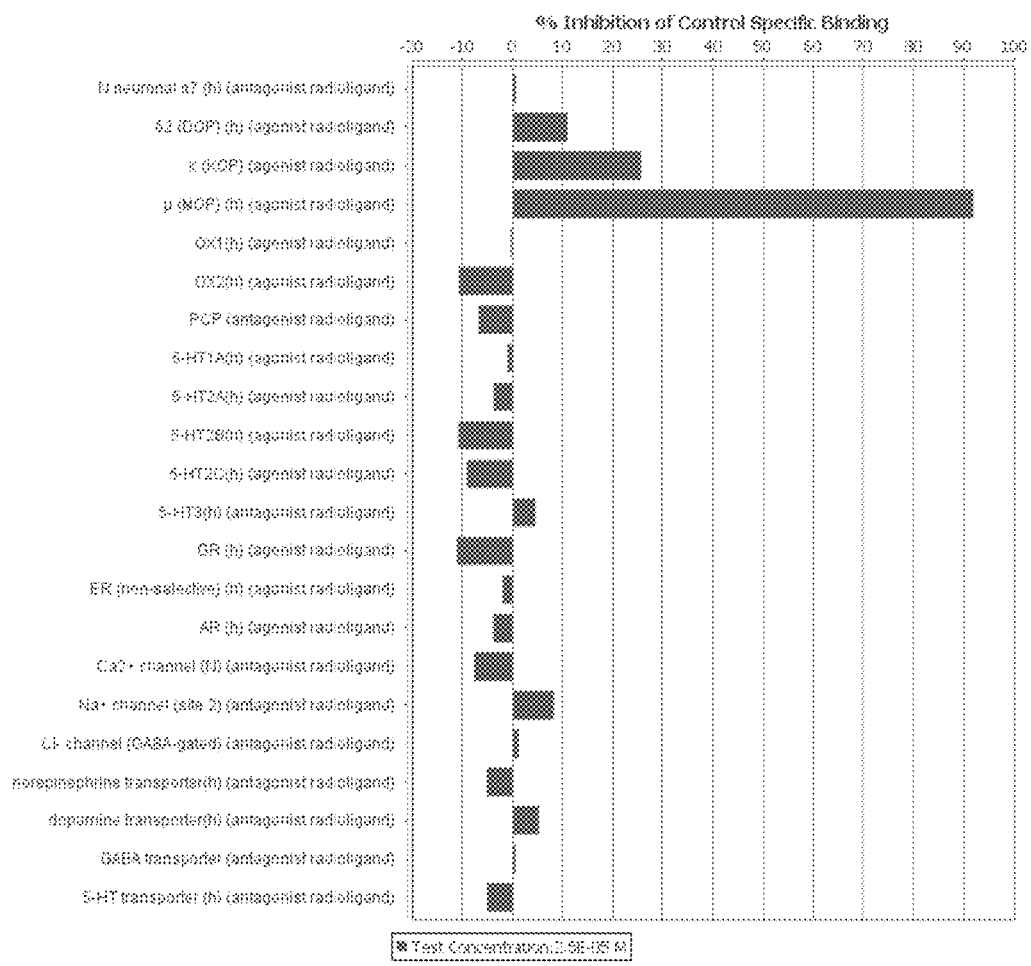
FIG. 6 is a histogram showing the results of an in vitro binding affinity screen performed on the second set of 22 targets to assess the abuse potential of Compound 1.
Figure 7:
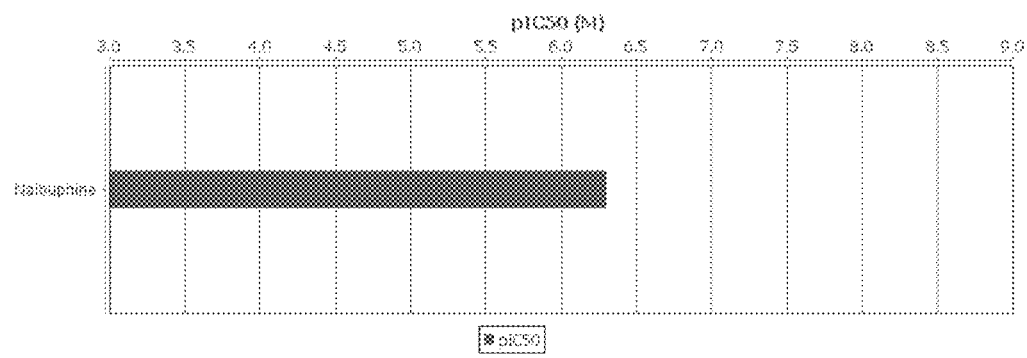
FIG. 7 is a histogram showing an $IC_{50}$ value of nalbuphine for inhibiting the binding of an agonist ligand of a δ-opioid receptor.
Figure 8:
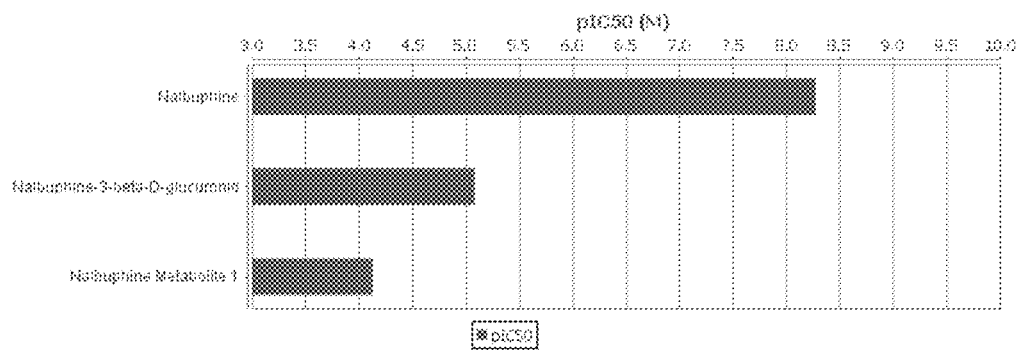
FIG. 8 is a histogram showing $IC_{50}$ values of nalbuphine, nalbuphine-3-beta-D-glucuronid, and Compound 1 for inhibiting the binding of an agonist ligand of a κ-opioid receptor.
Figure 9:
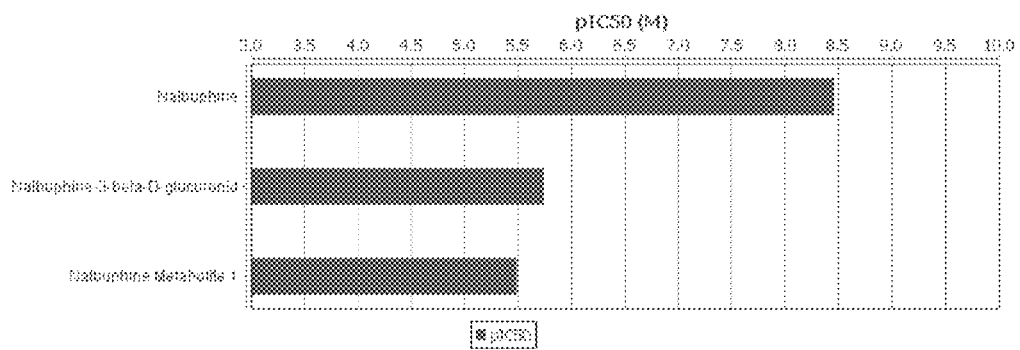
FIG. 9 is a histogram showing IC$_{50}$ values of nalbuphine, nalbuphine-3-beta-D-glucuronid, and Compound 1 for inhibiting the binding of an agonist ligand of a µ-opioid receptor.
Figure 10:
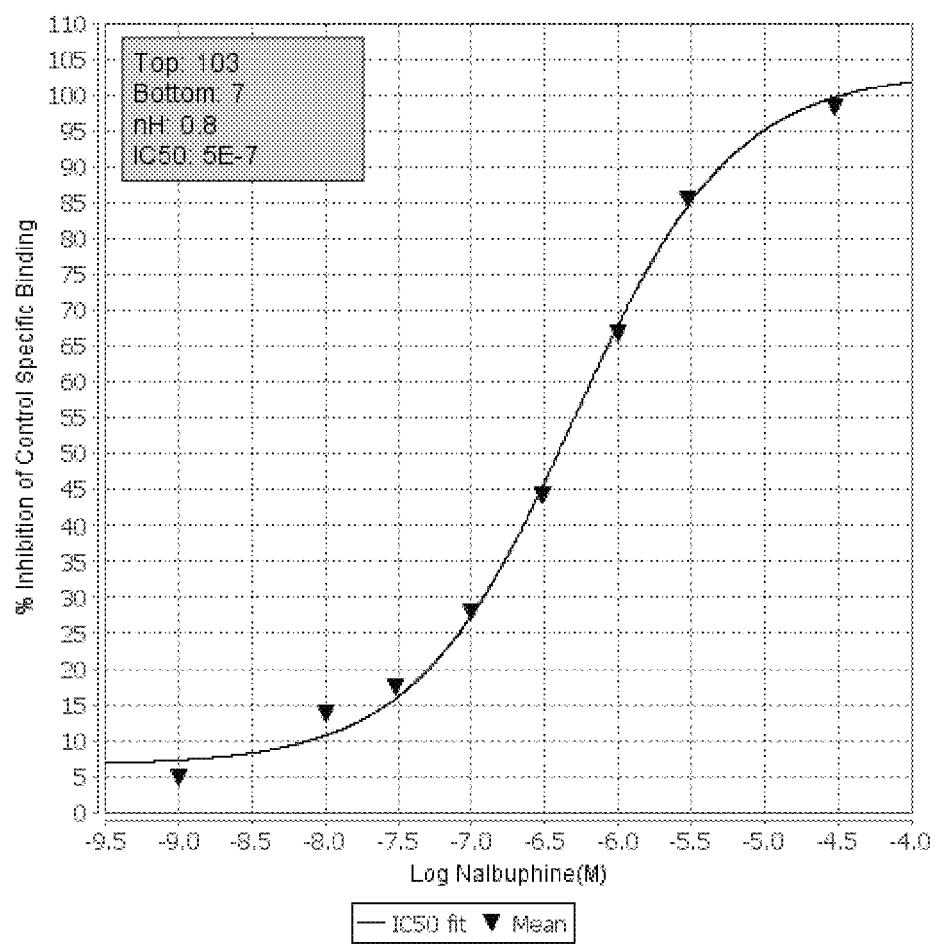
FIG. 10 is a graph showing % inhibition of the binding of an agonist ligand of a δ-opioid receptor by nalbuphine.
Figure 11:
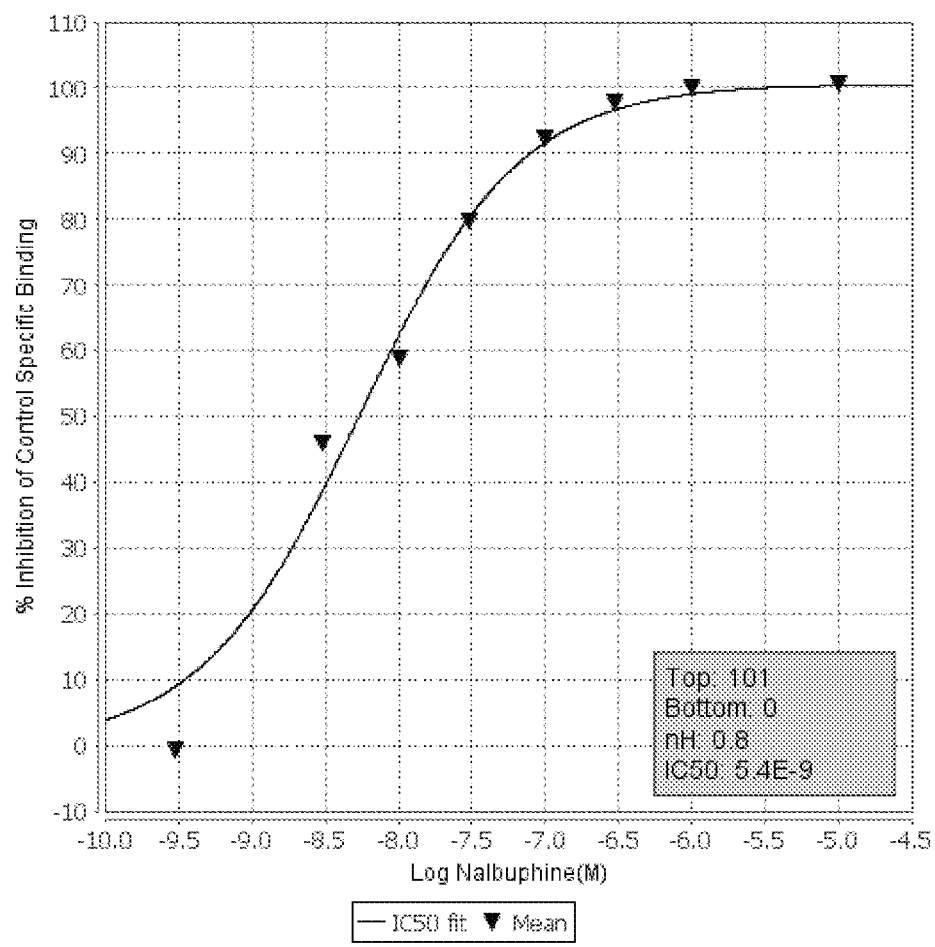
FIG. 11 is a graph showing % inhibition of the binding of an agonist ligand of a κ-opioid receptor by nalbuphine.
Figure 12:
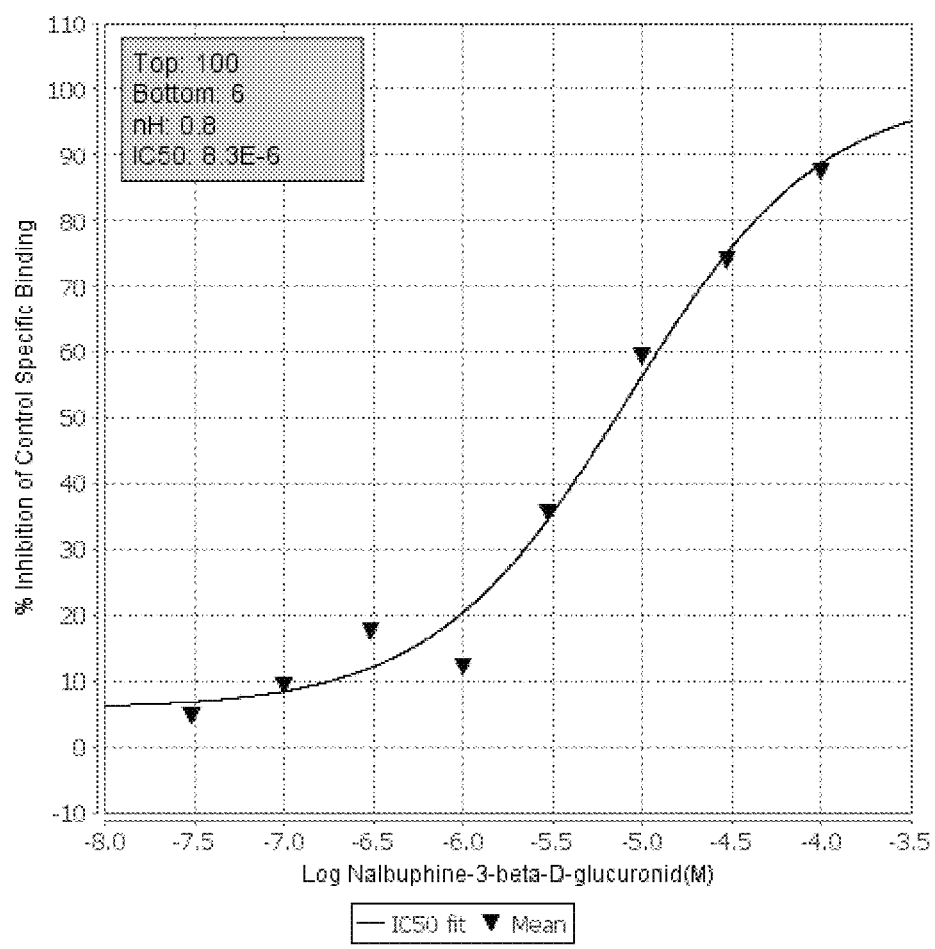
FIG. 12 is a graph showing % inhibition of the binding of an agonist ligand of a κ-opioid receptor by nalbuphine-3-beta-D-glucuronid.
Figure 13:
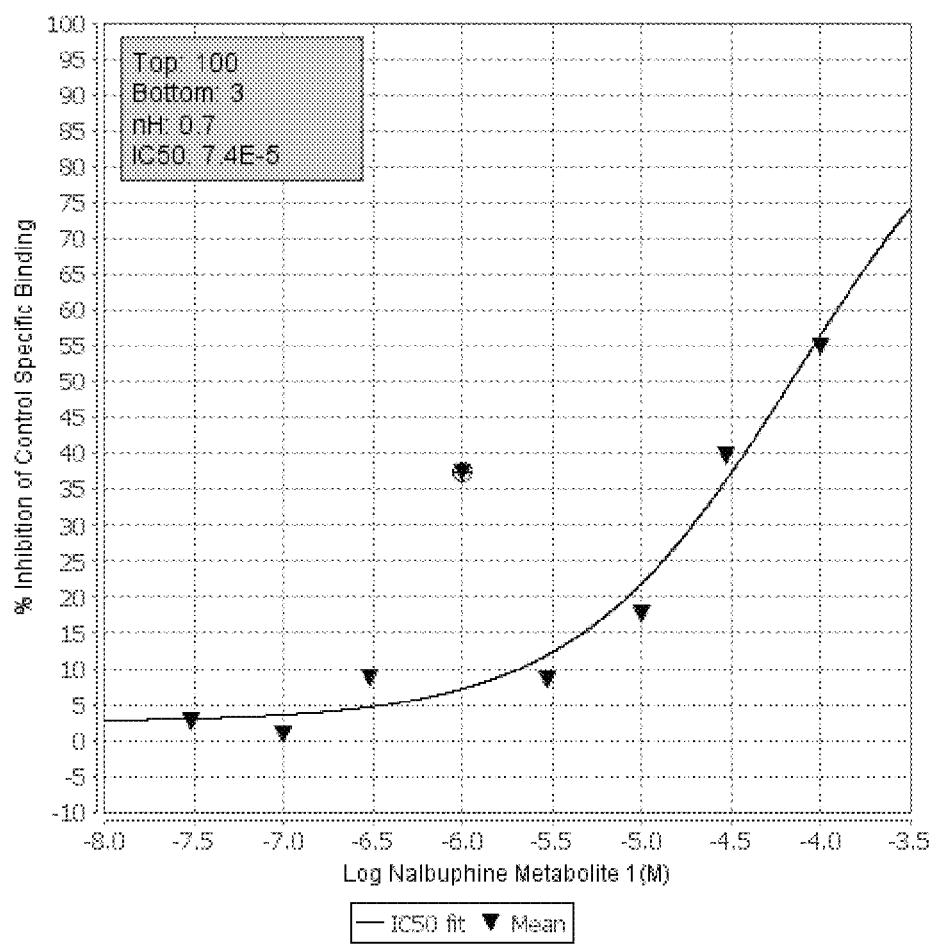
FIG. 13 is a graph showing % inhibition of the binding of an agonist ligand of a κ-opioid receptor by Compound 1.
Figure 14:
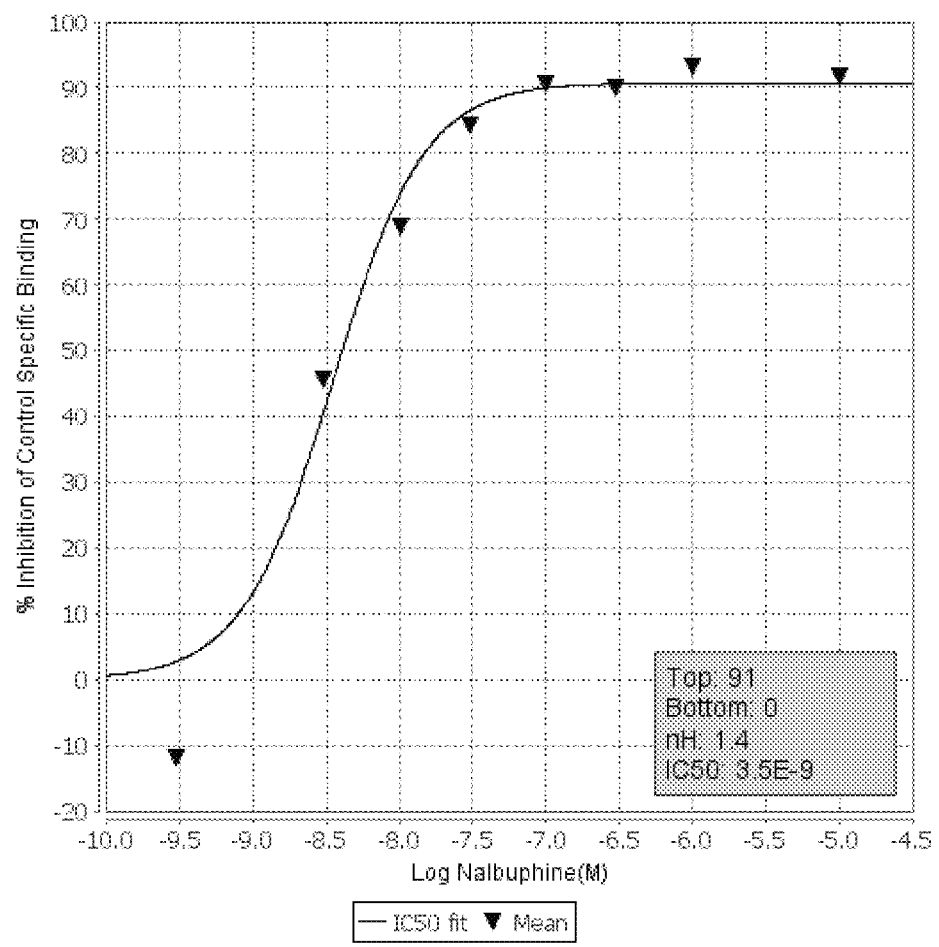
FIG. 14 is a graph showing % inhibition of the binding of an agonist ligand of a µ-opioid receptor by nalbuphine.
Figure 15:
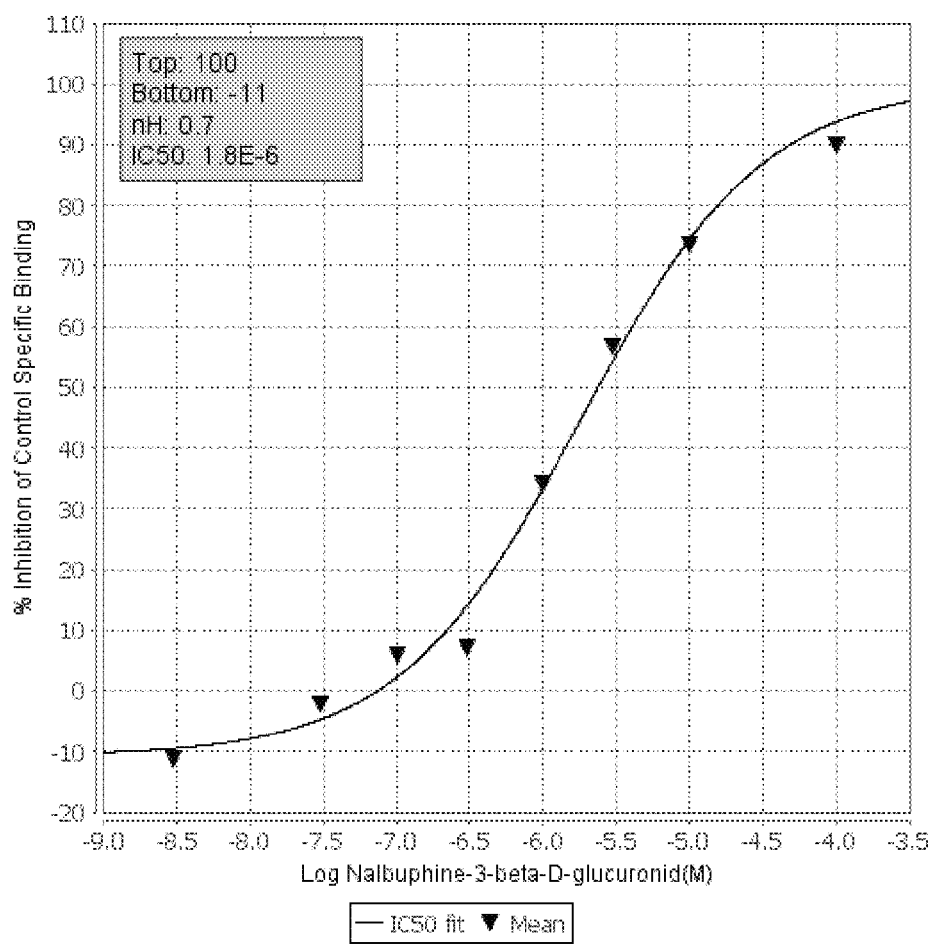
FIG. 15 is a graph showing % inhibition of the binding of an agonist ligand of a µ-opioid receptor by nalbuphine-3-beta-D-glucuronid.
Figure 16:
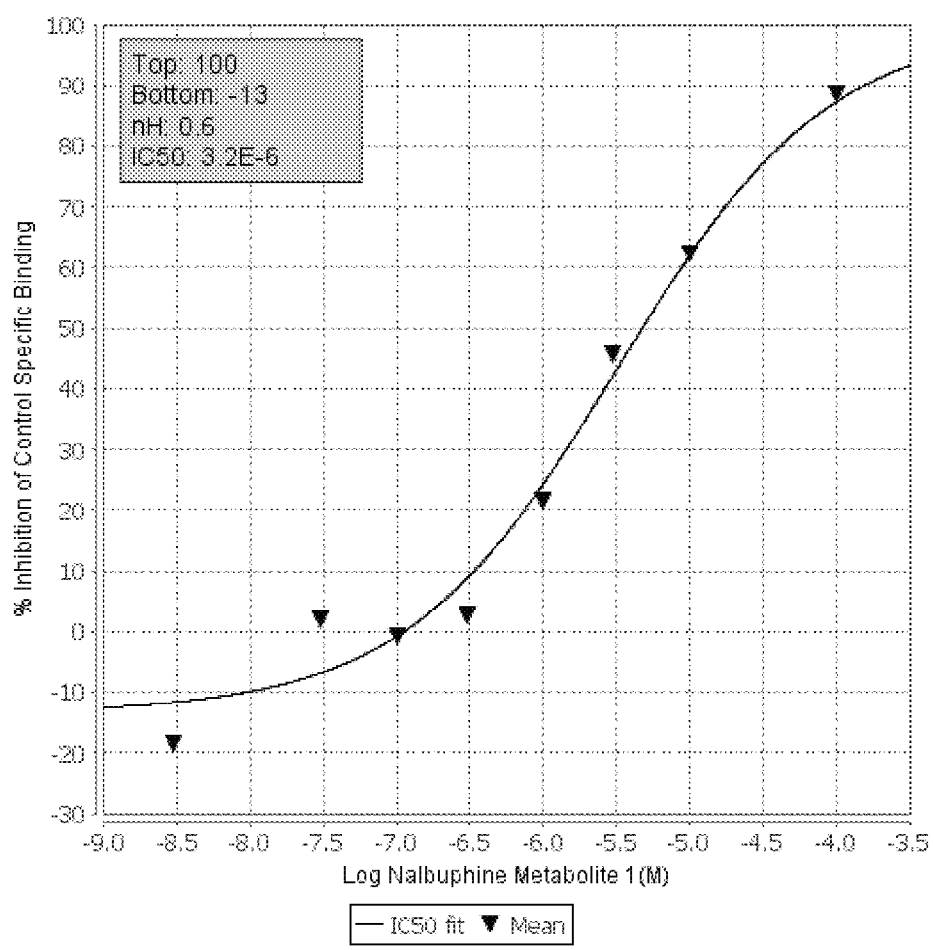
FIG. 16 is a graph showing % inhibition of the binding of an agonist ligand of a µ-opioid receptor by Compound 1.

These and other embodiments, advantages, and features of the present invention are provided in the sections below. Unless defined otherwise, all technical and scientific terms used herein have the same meaning as commonly understood by one of ordinary skill in the art to which this invention belongs.

DEFINITIONS

The terms "a" and "an" do not denote a limitation of quantity, but rather denote the presence of at least one of the referenced item. The terms "a" and "an" are used interchangeably with "one or more" or "at least one." The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±10%, ±5%, ±4%, ±3%, ±2%, ±1%, or ±less than 1%. Importantly, all recitations of a reference value preceded by the term "about" are intended to also be a recitation of the reference value alone. Furthermore, the phrases "less than about" or "greater than about" should be understood in view of the definition of the term "about" provided herein.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "substituted alkyl." The term "alkyl" also includes "cycloalkyl" which refers to a saturated or unsaturated cyclic alkyl radical containing from 3 to 10 ring atoms ($C_3$-$C_{10}$ cycloalkyl). Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 12 carbon atoms ($C_1$-$C_{12}$ alkyl). In still other embodiments, an alkyl group comprises from 1 to 6 carbon atoms ($C_1$-$C_6$ alkyl). It is noted that when an alkyl group is further connected to another atom, it becomes an "alkylene" group. In other words, the term "alkylene" refers to a divalent alkyl. For example, —$CH_2CH_3$ is an ethyl, while —$CH_2CH_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms ($C_1$-$C_{20}$ alkylene). In other embodiments, an alkylene group comprises from 1 to 12 carbon atoms ($C_1$-$C_{12}$ alkylene). In still other embodiments, an alkylene group comprises from 1 to 6 carbon atoms ($C_1$-$C_6$ alkylene).

The term "EC$_{50}$" as used herein refers to the concentration of a compound that gives half-maximal response. The term "IC$_{50}$" as used herein refers to the concentration of a compound where the response (or binding) is reduced by half.

The term "present compound(s)" or "compound(s) of the present invention" as used herein refers to compounds encompassed by structural formulae disclosed herein, e.g., formulae (I), (II), and (III), including any subgenus and specific compounds within these formulae, such as the compounds disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The term "tautomer" as used herein refers to isomers that change into one another with great ease so that they can exist together in equilibrium. In general, compounds may be hydrated or solvated. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

The term "lactone" or "lactone ring" refers to a saturated or unsaturated ring of two or more carbon atoms and a single oxygen atom with a ketone group at one of the carbons adjacent to the oxygen atom in the ring. The term "lactone" or "lactone ring" also includes substituted lactones. Typical lactones include, but are not limited to, α-acetolactone, β-propiolactone, γ-butyrolactone, δ-valerolactone, caprolactone, etc.; and the like. In some embodiments, the lactone group comprises from 3 to 10 ring atoms including the ring oxygen atom. In other embodiments, the lactone group comprises from 3 to 7 ring atoms including the ring oxygen atom.

The term "halogen" or "halo" as used herein includes fluoro (F), chloro (Cl), bromo (Br) and iodo (I) groups.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

The term "pharmaceutically acceptable" as used herein means suitable for use in contact with the tissues of humans and animals without undue toxicity, irritation, allergic response, and the like, commensurate with a reasonable benefit/risk ratio, and effective for their intended use within the scope of sound medical judgment.

"The term "salt" as used herein includes both acid and base addition salts. In one embodiment, the salt refers to a pharmaceutically acceptable salt. An acid addition salt refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A base addition salt refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The term "solvate" as used herein means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is a "hydrate." Examples of hydrate include, but are not limited to, hemihydrate, monohydrate, dihydrate, trihydrate, hexahydrate, etc. It should be understood by one of ordinary skill in the art that the present compound and/or the pharmaceutically acceptable salt of the present compound may also exist in a solvate form. The solvate is typically formed via hydration which is either part of the preparation of the present compound or through natural absorption of moisture by the anhydrous compound of the present invention.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"Substituted," when used to modify a specified group or radical, means that one or more hydrogen atoms of the specified group or radical are each, independently of one another, replaced with the same or different substituent(s).

Substituent groups useful for substituting saturated carbon atoms in the specified group or radical include, but are not limited to —$R^a$, halo, acyl, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, $S(O)_2O^-$, $S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^b$ $C(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Substituent groups from the above lists useful for substituting other specified groups or atoms will be apparent to those of skill in the art.

The substituents used to substitute a specified group can be further substituted, typically with one or more of the same or different groups selected from the various groups specified above.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the severity of the disorder, the size and health of the patient, and the route of administration. A skilled medical practitioner can readily determine the appropriate amount using methods known in the medical arts.

The term "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor. The pharmaceutical composition may be in various dosage forms or contain one or more unit dose formulations.

An "excipient" or "carrier" means a medium and/or composition suitable for administering the inventive compound in a dispersed/diluted form to mammals and/or suitable for use in contact with the tissues of humans and animals without undue toxicity, irritation, allergic response, and the like, commensurate with a reasonable benefit/risk ratio, and effective for their intended use within the scope of sound medical judgment.

The term "subject" includes, without limitation, a human or an animal. Exemplary animals include, but are not limited to, mammals such as mouse, rat, guinea pig, dog, cat, horse, cow, pig, monkey, chimpanzee, baboon, or rhesus monkey.

The term "treating" as used herein with regard to a subject, refers to improving at least one symptom of the subject's disease or disorder. Treating can be curing, improving, mitigating, and reducing the instances of a disease or condition, or the symptoms of a disease or condition, in addition to providing directions or prescribing a drug for such purpose.

Compounds

In one embodiment, the present invention provides a compound having structural Formula (I):

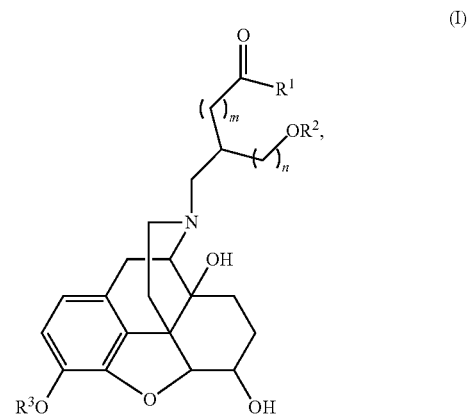

or a salt, solvate, or ester thereof, wherein $R^1$ is alkyl, $OR^4$, or $NR^5R^6$;

$R^2$ is H or alkyl; or alternatively, le and $OR^2$, together with the atoms to which they are attached, form a lactone ring;

m is 0 or 1;

n is 1 or 2; and $R^3$, $R^4$, $R^5$ and $R^6$ are independently hydrogen or alkyl.

In one embodiment of Formula (I), the compounds of Formula (I) is represented by a structural Formula (II):

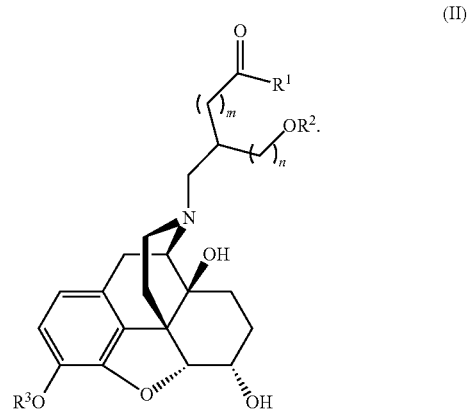

In one embodiment of Formula (I), le is OH, and both $R^2$ and $R^3$ are H.

In one embodiment of Formula (I), $R^2$ is H, and $R^3$ is alkyl.

In one embodiment of Formula (I), $R^2$ is alkyl, and $R^3$ is H.

In one embodiment of Formula (I), m is 1, and n is 1.

In one embodiment of Formula (I), m is 1, n is 1, $R^1$ is OH, $R^2$ is H, and $R^3$ is H.

In one embodiment of Formula (I), $R^1$ and $OR^2$, together with the atoms to which they are attached, form a lactone ring. In this embodiment, the compounds of Formula (I) have a structural Formula (III) or (III'):

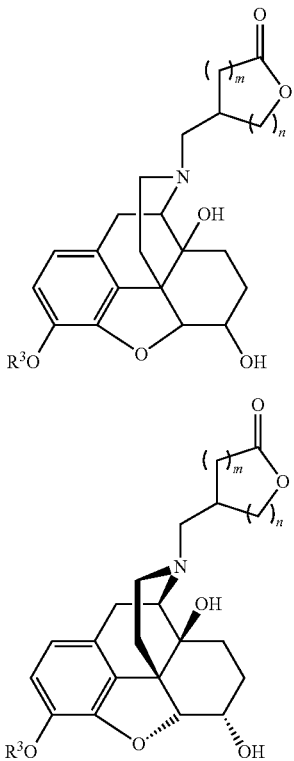

wherein $R^3$, m and n are as defined above.

In one embodiment of Formula (III) or (III'), m is 1, and n is 1.

In one embodiment of Formula (III) or (III'), m is 1, n is 1, and $R^3$ is H.

In one embodiment of Formula (III) or (III'), $R^3$ is alkyl.

In some specific embodiments of the present invention, the compound of Formula (I) is selected from the group consisting of:

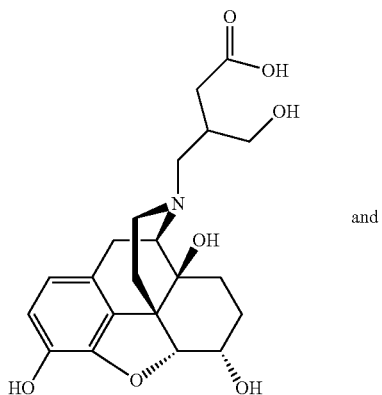

and

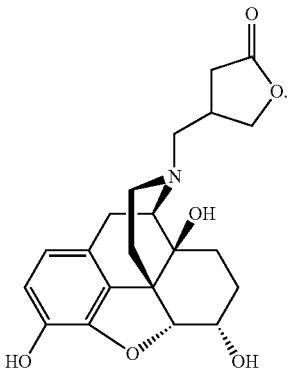

In one embodiment, the compounds of the present invention are in the form of any pharmaceutically acceptable salt or ester known in the art. Exemplary pharmaceutically acceptable salts include without limitation hydrochloric, sulfuric, nitric, phosphoric, hydrobromic, maleic, malic, ascorbic, citric, tartaric, pamoic, lauric, stearic, palmitic, oleic, myristic, lauryl sulfuric, napthalinesulfonic, linoleic, linolenic acid, and the like.

The present invention also includes pharmaceutically acceptable esters of the present compounds. The term "ester" denotes a derivative of the present compound containing an ester functional group which is capable of releasing the present compound when the ester form is administered to a subject. Release of the compound occurs in vivo. Pharmaceutically acceptable esters can be prepared by techniques known to one skilled in the art. These techniques generally modify appropriate functional groups in a given compound. These modified functional groups however regenerate original functional groups by metabolism of the compound in vivo. Esters include compounds wherein a hydroxy, amino, carboxylic, or a similar group is modified.

Suitable pharmaceutically acceptable esters for a hydroxyl group include inorganic esters such as phosphate esters and α-acyloxyalkyl ethers and related compounds which, as a result of in vivo hydrolysis of the ester, provide the parent hydroxy group. In vivo hydrolyzable ester forming groups for hydroxy include alkanoyl (e.g., $C_{1-10}$ linear, branched or cyclic alkyl), benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl.

Pharmaceutical Compositions and Dosage Forms

The present invention provides pharmaceutical compositions and dosage forms (including unit dosage forms) comprising a compound of the present invention or a salt, solvate, or ester thereof, and a pharmaceutically acceptable carrier or excipient. The compositions and dosage forms of the present invention are suitable for administration to subjects, e.g., humans and animals and include unit dosage forms, such as tablets, capsules, pills, powders, granules, sterile parenteral solutions or suspensions, and oral solutions or suspensions, and oil-water emulsions containing suitable quantities of the present compounds or a pharmaceutically acceptable salt, solvate or ester thereof.

Oral pharmaceutical dosage forms can be either solid or liquid. The solid dosage forms can be tablets, capsules, granules, and bulk powders. Types of oral tablets include compressed, chewable lozenges and tablets which can be enteric-coated, sugar-coated or film-coated. Capsules can be hard or soft gelatin capsules, while granules and powders can be provided in non-effervescent or effervescent form with the combination of other ingredients known to those skilled in the art. In other embodiments, the oral dosage form may be an osmotic-controlled release oral delivery system (OROS). In other embodiments, the oral dosage form may include matrix-embedded dosage forms or related devices. In some embodiments, the present oral dosage forms may include orally-disintegrating tablets.

Pharmaceutically acceptable carriers utilized in tablets include binders, lubricants, diluents, disintegrating agents, coloring agents, flavoring agents, and wetting agents.

Liquid oral dosage forms include aqueous solutions, emulsions, suspensions, solutions and/or suspensions reconstituted from non-effervescent granules and effervescent preparations reconstituted from effervescent granules.

Aqueous solutions include, for example, elixirs and syrups. Emulsions can be either oil-in water or water-in-oil. Elixirs are clear, sweetened, hydroalcoholic preparations. Pharmaceutically acceptable carriers used in elixirs include solvents. Syrups can be concentrated aqueous solutions of a sugar, for example, sucrose, and can contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions can use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, can include organic acids and a source of carbon dioxide. Coloring and flavoring agents can be used in all of the above dosage forms.

Parenteral administration of the formulations of the present invention includes intravenous, subcutaneous and intramuscular administrations of immediate, sustained (e.g., depot), extended, and/or modified release formulations (e.g., as described herein). Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

The concentration of the pharmaceutically active compound can be adjusted so that an injection provides an effective amount to produce the desired pharmacological effect. The exact dose depends on the age, weight and condition of the patient or animal, as is known in the art. The unit-dose parenteral preparations are packaged in an ampoule or a syringe with a needle. All preparations for parenteral administration must be sterile, as is known and practiced in the art. Illustratively, intravenous or intra-arterial infusion of a sterile aqueous solution containing the present compounds is an effective mode of administration.

Pharmaceutical dosage forms for rectal administration can be rectal suppositories, capsules and tablets for systemic effect. Rectal suppositories as used herein mean solid bodies for insertion into the rectum which melt or soften at body temperature releasing the pharmacologically and/or therapeutically active ingredients contained in the composition of this invention. Pharmaceutically acceptable substances utilized in rectal suppositories are bases or vehicles and agents to raise the melting point. Examples of bases include cocoa butter (theobroma oil), glycerin-gelatin, carbowax, polyoxyethylene glycol and mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

The compositions can be suspended in micronized or other suitable form or can be derivatized to produce a more soluble active product. The form of the resulting composition depends upon a number of factors, including the intended mode of administration and the solubility of the present compound in the selected carrier or vehicle. The effective concentration is sufficient for treating or alleviating pruritus, and can be empirically determined. The concentration is generally greater than the concentration for systemic administration of the compound.

The resulting mixture can be a solution, suspension, emulsion or the like, and can be formulated as a cream, gel, ointment, emulsion, solution, elixir, lotion, suspension, tincture, paste, foam, aerosol, irrigation, spray, suppository, bandage, or any other formulation suitable for topical or local administration. Modes of administration can include topical application to the skin, scalp, eyes, and/or nasal, buccal or sublingual mucosa.

Pharmaceutical and cosmetic carriers or vehicles suitable for administration of the compositions include any such carriers known to those skilled in the art to be suitable for the particular mode of administration. The present compounds can be included in the carriers in amounts sufficient to exert a therapeutically useful effect without serious toxic effects on the treated individual.

To formulate these compositions, a weight fraction of the present compound is dissolved, suspended, dispersed or otherwise mixed in a selected vehicle at an effective concentration such that the pruritic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream (USP), and hydrophilic ointment (USP).

In one embodiment, the invention provides topical compositions comprising an effective amount of compounds of Formula (I) and one or more cosmetically or pharmaceutically acceptable carriers or excipients for treating and/or relieving pruritus or itch. The term "cosmetically acceptable" as used herein means that the carriers or excipients are suitable for use in contact with tissues (e.g., the skin) and "pharmaceutically acceptable" means that the carriers or excipients are suitable for contact with tissues in which systemic adsorption is possible (e.g., mucosa, the gastrointestinal tract, etc.) without undue toxicity, incompatibility, instability, irritation, allergic response, and the like. In specific embodiments, topical compositions comprise an effective amount of Compound 1 or Compound 2 and one or more cosmetically or pharmaceutically acceptable carriers or excipients for treating and/or relieving pruritus or itch. The inventors have found that Compound 1 is a specific and weak partial agonist/antagonist of μ-opioid receptor and has an $EC_{50}$ of about 78,000 nM or about 70 μg/mL. Compound 1 is not lipophilic and is expected to be charged at physiologic pH due to an acidic side chain. Without wishing to be bound by any theory, it is expected that Compound 1 may not be partitioned readily across membranes and would be retained inside the skin.

Because the compounds of Formula (I), in particular Compound 1, is a weak μ-agonist/antagonist with a relatively high $EC_{50}$ value, these compounds can be formulated at concentrations far exceeding their $EC_{50}$ values to provide topical compositions effective for treating pruritic conditions. For instance, in some embodiments, topical compositions comprise from about 1 mg/mL to about 100 mg/mL, including values and ranges thereof, of compounds of Formula (I). In other embodiments, topical compositions comprise from about 0.1 mg/mL to about 100 mg/mL, including values and ranges thereof, of compounds of Formula (I).

In still other embodiments, topical compositions comprise about 0.1 mg/mL to about 10 mg/mL, about 0.1 mg/mL to about 20 mg/mL, about 0.1 mg/mL to about 50 mg/mL, about 0.1 mg/mL to about 100 mg/mL, about 0.5 mg/mL to about 10 mg/mL, about 0.5 mg/mL to about 20 mg/mL, about 0.5 mg/mL to about 30 mg/mL, about 0.5 mg/mL to about 40 mg/mL, about 0.5 mg/mL to about 50 mg/mL, about 0.5 mg/mL to about 60 mg/mL, about 0.5 mg/mL to about 70 mg/mL, about 0.5 mg/mL to about 80 mg/mL, about 0.5 mg/mL to about 90 mg/mL, about 0.5 mg/mL to about 100 mg/mL, about 0.5 mg/mL to about 150 mg/mL or about 0.5 mg/mL to about 200 mg/mL, including values and ranges thereof, of compounds of Formula (I). In some other embodiments, topical compositions comprise about 1 mg/mL to about 10 mg/mL, about 1 mg/mL to about 20 mg/mL, about 1 mg/mL to about 30 mg/mL, about 1 mg/mL to about 40 mg/mL, about 1 mg/mL to about 50 mg/mL, about 1 mg/mL to about 60 mg/mL, about 1 mg/mL to about 70 mg/mL, about 1 mg/mL to about 80 mg/mL, about 1 mg/mL to about 90 mg/mL, about 1 mg/mL to about 100 mg/mL, about 1 mg/mL to about 125 mg/mL, about 1 mg/mL to about 150 mg/mL, about 1 mg/mL to about 175 mg/mL, or about 1 mg/mL to about 200 mg/mL, including values and ranges thereof, of compounds of Formula (I).

In yet some other embodiments, topical compositions comprise about 5 mg/mL to about 15 mg/mL, about 5 mg/mL to about 25 mg/mL, about 5 mg/mL to about 40 mg/mL, about 5 mg/mL to about 50 mg/mL, about 5 mg/mL to about 60 mg/mL, about 5 mg/mL to about 70 mg/mL, about 5 mg/mL to about 80 mg/mL, about 5 mg/mL to about 90 mg/mL, about 5 mg/mL to about 100 mg/mL, about 5 mg/mL to about 125 mg/mL, about 5 mg/mL to about 150 mg/mL, about 5 mg/mL to about 175 mg/mL, or about 5 mg/mL to about 200 mg/mL, including values and ranges thereof, of compounds of Formula (I). In yet some other embodiments, topical compositions comprise about 10 mg/mL to about 50 mg/mL, about 10 mg/mL to about 60 mg/mL, about 10 mg/mL to about 70 mg/mL, about 10 mg/mL to about 80 mg/mL, about 10 mg/mL to about 90 mg/mL, about 10 mg/mL to about 100 mg/mL, about 10 mg/mL to about 125 mg/mL, about 10 mg/mL to about 150 mg/mL, about 10 mg/mL to about 175 mg/mL, or about 10 mg/mL to about 200 mg/mL, including values and ranges thereof, of compounds of Formula (I).

In some embodiments, topical compositions comprise from about 0.1% w/w to about 10% w/w, including values and ranges thereof, of compounds of Formula (I). In other embodiments, topical compositions comprise from about 0.5% w/w to about 50% w/w, including values and ranges thereof, of compounds of Formula (I).

In yet some other embodiments, topical compositions comprise about 0.5% w/w to about 10% w/w, about 0.5% w/w to about 20% w/w, about 0.5% w/w to about 30% w/w, about 0.5% w/w to about 40% w/w, about 0.5% w/w to about 50% w/w, about 0.5% w/w to about 60% w/w, about 0.5% w/w to about 70% w/w, about 0.5% w/w to about 80% w/w, about 0.5% w/w to about 90% w/w, including values and ranges thereof, of compounds of Formula (I). In yet some other embodiments, topical compositions comprise about 1% w/w to about 10% w/w, about 1% w/w to about 20% w/w, about 1% w/w to about 30% w/w, about 1% w/w to about 40% w/w, about 1% w/w to about 50% w/w, about 1% w/w to about 60% w/w, about 1% w/w to about 70% w/w, about 1% w/w to about 80% w/w, about 1% w/w to about 90% w/w, including values and ranges thereof, of compounds of Formula (I). In yet some other embodiments, topical compositions comprise about 5% w/w to about 10% w/w, about 5% w/w to about 20% w/w, about 5% w/w to about 30% w/w, about 5% w/w to about 40% w/w, about 5% w/w to about 50% w/w, about 5% w/w to about 60% w/w, about 5% w/w to about 70% w/w, about 5% w/w to about 80% w/w, about 5% w/w to about 90% w/w, including values and ranges thereof, of compounds of Formula (I).

The topical compositions include, but are not limited to, solutions, lotions, creams, gels, sticks, sprays, ointments, emulsions (e.g., microemulsions and nanoemulsions), dispersions (e.g., microdispersions and nanodispersions), extended release dosage forms, orally disintegrating tablets, cleansing liquid washes, solid bars, shampoos, pastes, foams, powders, mousses, shaving creams, wipes, patches, nail lacquers, wound dressing, adhesive bandages, hydrogels, and films. These product types may comprise several types of cosmetically acceptable topical carriers including, but not limited to solutions, suspensions, emulsions (e.g., microemulsions and nanoemulsions), dispersions (e.g., microdispersions and nanodispersions) gels, solids and liposomes.

In various embodiments, the topical compositions comprising the compounds of Formula (I) can be delivered topically to various tissues or organs including, but not limited to, the skin, scalp, eyes, nasal mucosa, buccal mucosa, sublingual mucosa and/or gastrointestinal tract. In specific embodiments, the compositions delivered topically to various tissues or organs comprise Compound 1 or Compound 2.

In some embodiments, compositions of the present invention are suitable for topical administration of the compounds of Formula (I) to the gastrointestinal (GI) tract, for example the upper and lower gastrointestinal tract including, but not limited to, the small and large intestines. In these embodiments, compositions comprising the compounds of Formula (I) could be administered orally for topical or local delivery to the GI tract. Topical or local delivery of the compounds of Formula (I) to the GI tract is desirable for treating gastrointestinal conditions including, but not limited to, diarrhea, gastroenteritis, inflammatory bowel disease and short bowel syndrome. In specific embodiments, the compositions delivered topically to the GI tract comprise Compound 1 or Compound 2. The compositions intended for topical delivery of the compounds of Formula (I) to the gastrointestinal (GI) tract include, but are not limited to, extended release (ER) dosage forms and orally disintegrating tablets (ODT).

In certain embodiments, compositions comprising the compounds of Formula (I) that are delivered topically to various tissues or organs have no significant systemic activity after administration. The term "no significant systemic activity", as used herein refers to compositions which do not provide a generalized effect in the body through absorption into the circulation, but do provide local effects through topical contact with a diseased tissue.

In some embodiments, the compositions employed in the present methods can relieve pruritus when applied to the skin. The composition can be administered topically to the affected area up to eight times per day, as needed, to provide reduction in and relief from itching. Relief can be temporary or permanent, and can even be evident after a single dose of the composition. When the composition is administered in a form other than a topical preparation, it should be administered in an amount sufficient to provide relief from pruritus that is within safety guidelines established by the FDA. Determining the appropriate amount to administer to a patient is within the skill of the person of ordinary skill in the art in association with teachings provided by the present invention.

In some embodiments, topical compositions of the present invention are used for the treatment of a subject suffering from itch or a pruritic condition associated with a skin change. For example, such pruritic condition can be selected from the group consisting of pruritus secondary to inflamed skin (e.g., atopic dermatitis, psoriasis, burns); pruritus arising from conditions of non-diseased skin (e.g., uremic pruritus, cholestatic pruritus, cancers, hydroxyetheyl starch induced pruritus), and pruritus associated with chronic secondary scratch or other types of skin lesions that may or may not be the result of an underlying medical condition (e.g., prurigo nodularis).

Solutions of the compositions of this invention intended for topical administration contain an amount of the composition effective to deliver an anti-pruritic amount, typically at a concentration of between about 0.01% w/w to about 5% w/w. The balance of the solution is water, a suitable organic solvent or other suitable solvent or buffer. These compositions that are formulated as solutions or suspensions can be applied to the skin, or can be formulated as an aerosol or foam and applied to the skin as a spray-on. The aerosol compositions typically contain from 25% to 80% w/w, preferably from 30% to 50% w/w, of a suitable propellant. Gel compositions can be formulated by simply admixing a suitable thickening agent to the solution or suspension.

Solutions and suspensions can also be topically applied to the eyes and mucosa. Solutions, particularly those intended for opthalmic use, can be formulated as 0.01%-10% w/w isotonic solutions, pH about 5-7, with appropriate salts, and preferably containing one or more of the compositions herein at a concentration of about 0.1% w/w, up to about 5% w/w or more. Suitable ophthalmic solutions are known in the art.

Compositions of solid forms intended for topical application can be formulated as stick-type compositions intended for application to the lips or other parts of the body. Such compositions contain an effective amount of the present compounds or a pharmaceutically acceptable salt, solvate or ester thereof. The amount of the present compound is typically from about 0.01% w/w to about 5% w/w. The solids also contain from about 40% to 98% w/w, preferably from about 50% to 90% w/w, of emollients. This composition can further contain from 1% to 20% w/w, preferably from 5% to 15% w/w, of a suitable thickening agent, and, if desired or needed, emulsifiers and water or buffers.

In addition, the compositions, and preparations containing the compositions, can also be coated on bandages, mixed with bioadhesives, or included in dressings. Thus, combinations of bandages, bioadhesives, dressings and other such materials and the compositions formulated as described herein are provided.

In one embodiment, pharmaceutical compositions or dosage forms according to the invention are prepared in the form of oral sustained release formulations. The sustained release formulation of the present invention comprises a therapeutically effective amount of the compound of Formula (I) or a pharmaceutically acceptable salt, solvate or ester thereof. The oral sustained release formulations can provide a controlled release of the drug over a longer period than observed for bolus injections or immediate release oral formulations (e.g., at least about 8-12 hours). Reducing the frequency of dosing provides the potential for enhanced patient convenience and compliance with the present methods. The lower dosing frequency also has the potential to provide reduced side effects because the patient may be exposed to lower peak concentrations of drug over time.

The present invention also provides compositions including the compound of Formula (I) or a pharmaceutically acceptable salt, solvate or ester thereof and a sustained release delivery system. The sustained release delivery system may contain a hydrophilic compound, a cross-linking agent, and a diluent. Alternatively, the sustained release delivery system may employ a hydrophobic compound.

In some embodiments, the compound of Formula (I), Formula (II), Formula (III), Formula (III'), or Compound 1 or Compound 2 of the invention is present in the composition in an amount of about 1 mg to about 240 mg; about 1 mg to about 150 mg; about 1 mg to about 125 mg; or about 1 mg to about 100 mg. In some embodiments, the compound is present in the composition in an amount of about 5 mg to about 60 mg; about 5 mg to about 80 mg; about 10 mg to about 70 mg; about 15 mg to about 60 mg; about 40 mg to about 80 mg; about 50 mg to about 70 mg; or about 45 mg to about 60 mg. In one embodiment, the compound is present in the composition in an amount of about 5 mg, about 10 mg, about 15 mg, about 20 mg, about 25 mg, about 30 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, or about 240 mg. In another embodiment, the compound is present in the composition in an amount of about 15 mg, about 30 mg, about 45 mg, about 60 mg, about 120 mg, or about 180 mg. In yet another embodiment, the compound is present in the composition in an amount of about 15 mg, 30 mg, 90 mg, 120 mg or 180 mg.

The compound of Formula (I), Formula (II), Formula (III), Formula (III'), or Compound 1 or Compound 2 of the invention can be provided in isolated form at a purity of at least about 75%, for example about 75%, about 76%, about 77%, about 78%, about 79%, about 80%, about 81%, about 82%, about 83%, about 84%, about 85%, about 86%, about 87%, about 88%, about 89%, 90%, about 91%, about 92%, about 93%, about 94%, about 95%, about 96%, about 97%, about 98%, about 98.5%, about 99%, about 99.5%, about 99.6%, about 99.7%, about 99.8%, about 99.9%, or about 100%. In any of the pharmaceutical compositions described herein, The compound of Formula (I), Formula (II), Formula (III), Formula (III'), or Compound 1 or Compound 2 of the invention can be provided in the pharmaceutical composition at a purity of at least about 90% (excluding the excipients), for example about 90%, about 91%, about 92%, about 93%, about 94%, about 95%, about 96%, about 97%, about 98%, about 98.5%, about 99%, about 99.5%, about 99.6%, about 99.7%, about 99.8%, about 99.9%, or about 100%.

The sustained release delivery system may include at least one hydrophilic compound. The hydrophilic compound preferably forms a gel matrix that releases the compound of the invention at a sustained rate upon exposure to liquids. The rate of release of the compound from the gel matrix depends on the drug's partition coefficient between the components of the gel matrix and the aqueous phase within the gastrointestinal tract. The weight ratio of the compound of the invention to the hydrophilic compound is generally in the range of about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, and about 2:1 to about 1:2. In some embodiments, the weight ratio of the compound of the invention to the hydrophilic compound is in the range of about 10:1 to about 1:1, about 10:1 to about 2:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, and about 2:1 to about 1:1. In some embodiments, the weight ratio of the compound of the invention to the hydrophilic compound is in the range of about 6:1 to about 1:1, about 5:1 to about 2:1, about 4:1 to about 3:1, about 4:1 to about 2:1, and about 5:1 to about 2:1. In some embodiments, the weight ratio of the compound of the invention to the hydrophilic compound is about 1:5, about 1:4.5, about 1:4.4, about 1:4, about 1:3.5, about 1:3.3, about 1:3, about 1:2.5, about 1:2, about 1:1, and about 1:1.5.

The sustained release delivery system generally includes the hydrophilic compound in an amount of about 5% to about 80% by weight. In some embodiments, the sustained release delivery system generally includes the hydrophilic compound in an amount of about 5% to about 30%, about 8% to about 31%, about 10% to about 20%, about 20% to about 60%, or about 40% to about 60% by weight. In one embodiment, the sustained release delivery system includes the hydrophilic compound in an amount of about 8% to about 31% by weight. In one embodiment, the sustained release delivery system includes the hydrophilic compound in an amount of about 10% to about 20% by weight. In some embodiments, the sustained release delivery system includes the hydrophilic compound in an amount of about 10%, about 11%, about 12%, about 13%, about 14%, about 15%, about 16%, about 17%, about 18%, about 19%, or about 20% by weight. In one embodiment, the sustained release delivery system includes the hydrophilic compound in an amount of about 12% by weight. In one embodiment, the sustained release delivery system includes the hydrophilic compound in an amount of about 8% by weight. In one embodiment, the sustained release delivery system includes the hydrophilic compound in an amount of about 20% by weight. In one embodiment, the sustained release delivery system includes the hydrophilic compound in an amount of about 28% by weight.

The hydrophilic compound is any compound known in the art to be hydrophilic. Exemplary hydrophilic compounds include without limitation gums, cellulose ethers, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. In some embodiments, the hydrophilic compound is a gum. In other embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum.

In another aspect, the sustained release delivery system further includes at least one cross-linking agent. In one embodiment, the cross-linking agent is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally includes the cross-linking agent in an amount of about 0.5% to about 80% by weight. In one embodiment, the sustained release delivery system generally includes the cross-linking agent in an amount of about 12% to about 47% by weight. In another embodiment, the sustained release delivery system generally includes the cross-linking agent in an amount of about 20% to about 30% by weight. In one embodiment, the sustained release delivery system generally includes the cross-linking agent in an amount of about 15% to about 25% by weight. In some embodiments, the at least one cross-linking agent is present in the sustained release delivery system in an amount of about 15%, about 16%, about 17%, about 18%, about 19%, about 20%, about 21%, about 22%, about 23%, about 24%, or about 25% by weight. In one embodiment, the sustained release delivery system includes the cross-linking agent in an amount of about 18% by weight. In one embodiment, the sustained release delivery system includes the cross-linking agent in an amount of about 12% by weight. In one embodiment, the sustained release delivery system includes the cross-linking agent in an amount of about 30% by weight. In one embodiment, the sustained release delivery system includes the cross-linking agent in an amount of about 42% by weight.

Exemplary cross-linking agents include homopolysaccharides. Exemplary homopolysaccharides include without limitation galactomannan gums, such as guar gum, hydroxypropyl guar gum, and locust bean gum. In some embodiments, the cross-linking agent is a locust bean gum or a guar gum. In other embodiments, the cross-linking agent is an alginic acid derivative or hydrocolloid.

In some embodiments, when the sustained release delivery system includes at least one hydrophilic compound and at least one cross-linking agent, the weight ratio of hydrophilic compound to cross-linking agent is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1. In some embodiments, the weight ratio of hydrophilic compound to cross-linking agent is about 1:5, about 1:4.5, about 1:4, about 1:3.5, about 1:3, about 1:2.5, about 1:2, about 1:1.5, and about 1:1.

The sustained release delivery system may include one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof.

In some embodiments, the sustained release compositions are further admixed with one or more wetting agents (e.g., polyethoxylated castor oil, polyethoxylated hydrogenated castor oil, polyethoxylated fatty acid from castor oil, polyethoxylated fatty acid from hydrogenated castor oil) one or more lubricants (e.g., magnesium stearate, sodium stearyl fumarate, and the like), one or more buffering agents, one or more colorants, and/or other conventional ingredients.

Pruritic Conditions and Treatment Methods

The present invention provides methods for treating a pruritic condition by administering an effective amount, e.g., an effective amount of a compound of the invention or an effective amount of a sustained release formulation comprising a compound of the invention to a subject, e.g., human or animal patient in need thereof. An effective amount is an amount sufficient to eliminate or significantly reduce symptoms of the pruritic condition or to alleviate those symptoms (e.g., reduce the symptoms, such as itching, compared to the symptoms present prior to administration of the compound of the invention). "Sustained release" or "extended release" means that the compound is released from the formulation at a controlled rate so that therapeutically beneficial blood levels (but below toxic levels) of the compound are maintained over an extended period of time. Alternatively, "sustained release" or "extended release" means that the desired pharmacologic effect is maintained over an extended period of time.

In some embodiments, the method for treating a pruritic condition comprises administering a compound of the invention to a subject in need thereof at a dose of about 5 mg to about 60 mg. In some embodiments, the method for treating a pruritic condition comprises administering a composition or a dosage form comprising about 5 mg to about 60 mg of the compound of the invention to a subject in need thereof.

In some embodiments, the compounds and/or the compositions of the invention provide an anti-pruritic effect over a period of at least about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours. In some embodiments, the invention provides an anti-pruritic effect over a period of about 6-18 hours, about 8-16 hours, about 8-12 hours, about 8 to about 24 hours, about 12 to about 24 hours, about 18 to about 24 hours, or about 8-10 hours. In some other embodiments, the invention provides an anti-pruritic effect over a period of about 1 day, 2 days, 3 days, 4 days or more. In some embodiments, the itchy sensation does not return after certain treatment period.

According to the present invention, pruritus includes any itchy or pruritic condition, e.g., a sensation that causes the desire or reflex to scratch. In some embodiments, compounds of the present invention are used for the treatment of a subject suffering from a pruritic condition selected from the group consisting of atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticarial, prurigo, herpes, impetigo, eczema, tinea, lichen, psoriasis, scabies and acne vulgaris, visceral diseases complicated with pruritus such as malignant tumors, diabetes mellitus, hepatic diseases, renal failure, hemodialysis, peritoneal dialysis, and pregnancy.

In some embodiments, compounds of the present invention are used for the treatment of a subject suffering from a pruritic condition associated with a skin change. For example, such pruritic condition can be selected from the group consisting of pruritus secondary to inflamed skin (e.g., atopic dermatitis, psoriasis, burns); pruritus arising from conditions of non-diseased skin (e.g., uremic pruritus, cholestatic pruritus, cancers, hydroxyethyl starch induced pruritus), and pruritus associated with chronic secondary scratch or other types of skin lesions that may or may not be the result of an underlying medical condition (e.g., prurigo nodularis) and the underlying disease is categorized based on histological, radiological or other investigations as being of an origin selected from the group consisting of dermatologic origin, systemic disease origin, neurologic origin, psychogenic origin, mixed origin, or other origin.

In some embodiments, compounds of the present invention are used for the treatment of a subject suffering from a pruritic condition associated with neurogenic inflammation of the skin, e.g., prurigo nodularis, atopic dermatitis, burn pruritus, burn, wound healing, etc. In some other embodiments, methods of the present invention are used for the treatment of a subject suffering from a pruritic condition associated with neurogenic inflammation with elevated substance P level. In still some other embodiments, methods of the present invention are used for the treatment of a subject suffering from a pruritic condition associated with elevated substance P level.

In some embodiments, methods of the present invention are used for the treatment of a subject suffering from a pruritic condition associated with one or more related or unrelated conditions. For example, the pruritic condition can be associated with a dermatologic condition including aquagenic pruritus, atopic dermatitis, idiopathic pruritus, Lichen simplex chronicus, prurigo nodularis, psoriasis, and scabies. In another example, the pruritic condition can be associated with a hematological or oncological condition including cancer related pruritus, chemotherapy induced pruritus, HIV protease inhibitor induced pruritus, Hodgkin's lymphoma associated pruritus, polycythemia vera, etc. In another example, the pruritic condition can be associated with a metabolic condition including cholestatic pruritus, uremic pruritus, etc. In still another example, the pruritic condition can be associated with a condition of pain or neurological condition including brachioradial pruritus, burn induced pruritus, neuropathic pruritus, morphine induced pruritus, multiple sclerosis associated pruritus, post herpetic pruritus, pruritus associated with psychiatric causes, etc.

In one embodiment, methods of the present invention are used for the treatment of uremic pruritus. In another embodiment, methods of the present invention are used for the treatment of prurigo nodularis. In yet another embodiment, methods of the present invention are used to treat human beings. In still another embodiment, methods of the present invention are used to treat animals other than human beings.

Preparations

The starting materials used in preparing the compounds of the invention, i.e. the various structural subclasses and species of the compounds of the synthetic precursors of the present compounds of Formula (I), are often known compounds, or can be synthesized by known methods described in the literature, or are commercially available from various sources well known to those of ordinary skill in the art, such as for example, Sigma-Aldrich Corporation of St. Louis, Mo. USA and their subsidiaries Fluka and Riedel-de Haen, at their various other worldwide offices, and other well known chemical suppliers such as Fisher Scientific, TCI America of Philadelphia, Pa., ChemDiv of San Diego, Calif., Chembridge of San Diego, Calif., Asinex of Moscow, Russia, SPECS/BIOSPECS of the Netherlands, Maybridge of Cornwall, England, Acros, TimTec of Russia, Comgenex of South San Francisco, Calif., and ASDI Biosciences of Newark, Del.

It is recognized that the skilled artisan in the art of organic chemistry can readily carry out the synthesis of many starting materials and subsequent manipulations without further direction, that is, it is well within the scope and practice of the skilled artisan to carry out many desired manipulations. These include reduction of carbonyl compounds to their corresponding alcohols, oxidations, acylations, aromatic substitutions, both electrophilic and nucleophilic, etherifications, esterification, saponification, nitrations, hydrogenations, reductive animation and the like. These manipulations are discussed in standard texts such as March's Advanced Organic Chemistry (3d Edition, 1985, Wiley-Interscience, New York), Feiser and Feiser's Reagents for Organic Synthesis, and in the various volumes and editions oiMethoden der Organischen Chemie (Houben-Weyl), and the like. Many general methods for preparation of starting materials comprising variously substituted heterocyclic, hetereoaryl, and aryl rings (the precursors of Ar, hAr$^1$, and/or hAr$^2$) can be found in Methoden der Organischen Chemie (Houben-Weyl), whose various volumes and editions are available from Georg Thieme Verlag, Stuttgart. The entire disclosures of the treatises recited above are hereby incorporated by reference in their entireties for their teachings regarding methods for synthesizing organic compounds and their precursors.

The skilled artisan will also readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts, Protecting Groups in Organic Synthesis, 3$^r$ Ed., John Wiley & Sons (1999).

An exemplary synthetic method for preparing the present compounds is illustrated in Scheme 1 below. Compound 1 is identified as 6 and Compound 2 is identified as lactone 5 in the scheme.

Scheme 1: Synthesis of Compound 1

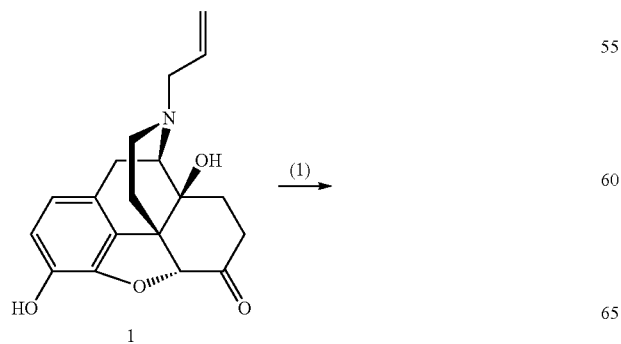

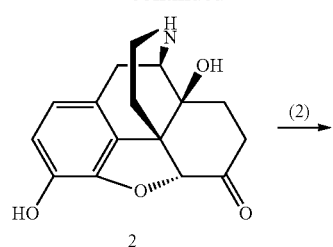

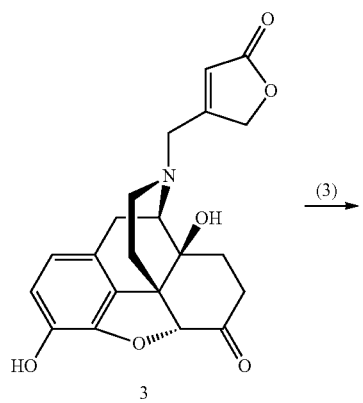

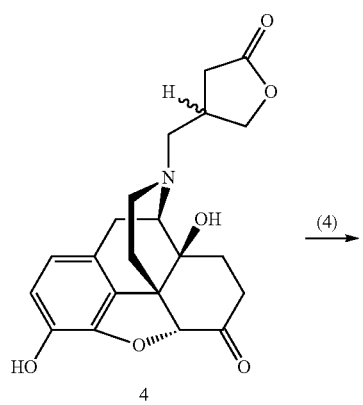

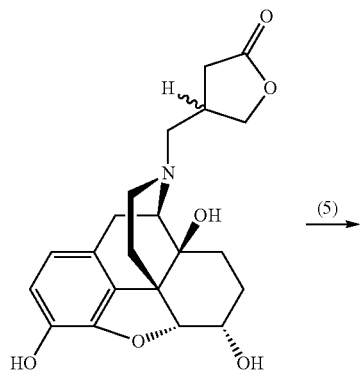

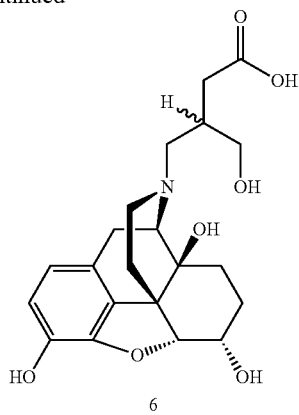

6

Synthesis of Noroxymorphone Hydrochloride (2):

Five separate CEM 10-mL microwave reaction vessels equipped with magnetic stir bars were each charged with naloxone hydrochloride 1 (500 mg, 1.4 mmol) followed by a 2:1 v/v mixture of water/1,4-dioxane (6.0 mL). Wilkinson's catalyst (67 mg, 0.07 mmol) was added to the vessels and nitrogen gas was bubbled through the reaction mixtures for 10 minutes at room temperature. The reaction vessels were then sealed and heated sequentially with stirring to 150° C. for 1 hour in a CEM Discover benchtop microwave reactor. The vessels were then cooled to room temperature and insoluble material was removed by filtration through a short plug of Celite. The pooled filtrates were then concentrated to a solid using a rotary evaporator to afford the product, noroxymorphone (2, 3.25 g, 99% yield), as a hydrochloride salt that was used without additional purification. $^1$H NMR (400 MHz, DMSO-d6) δ ppm 1.36-1.52 (m, 2H) 1.89-1.98 (m, 1H) 2.05-2.15 (m, 1H) 2.56 (dd, J=12.71, 4.27 Hz, 1H) 2.88-3.11 (m, 3H) 3.20-3.30 (m, 1H) 3.68 (d, J=5.71 Hz, 1H) 4.93 (s, 1H) 6.46 (s, 1H) 6.58-6.73 (m, 2H) 9.45 (s, 1H) MS (ESI) m/z 288 [M+H$^+$].

Synthesis of Butenolide Intermediate (3):

A 250-mL RB-flask equipped with a magnetic stirrer was placed under a nitrogen atmosphere and charged with noroxymorphone HCl 2 (1.502 g, 4.65 mmol) followed by N,N-dimethylformamide (150 mL). Solid sodium bicarbonate (1.95 g, 23.2 mmol) was then added to the reaction flask in a single portion. To this mixture was added 4-bromomethyl-2,5-dihydrofuran-2-one (0.329 g, 1.86 mmol) in a dropwise fashion via syringe. Upon completion of addition of the bromide, the reaction was heated to 70° C. and stirred vigorously at this temperature. Over the course of 4 hours, additional 4-bromomethyl-2,5-dihydrofuran-2-one (0.329 g, 1.86 mmol) was added two times to the reaction mixture to give a total of 5.58 mmol (1.2 molar equivalents) of the bromide electrophile. After 4 total hours of stirring at 70° C., the reaction was cooled to ambient temperature and diluted with chloroform (250 mL). The resulting solution was washed with saturated aqueous sodium chloride (500 mL). The organics were then washed sequentially with water (250 mL) and saturated aqueous lithium chloride (2×250 mL). The organic extract was then dried over sodium sulfate and concentrated to dryness using a rotary evaporator. The resulting residue was purified by normal phase chromatography using a 120-gram Isco silica gel column. The column was eluted with dichloromethane (A) and a 95:5 v/v solution of dichloromethane/methanol (B) with a 0-60% gradient over 45 minutes to afford an amber oil (1.46 g) comprised of the crude product (3) along with some residual N,N-dimethylformamide. The material was used in the next step without additional purification. $^1$H NMR (400 MHz, DMSO-d6) δ ppm 1.21-1.32 (m, 1H) 1.38-1.55 (m, 1H) 1.71-1.83 (m, 1H) 2.00-2.13 (m, 2H) 2.35-2.48 (m, 2H) 2.53-2.60 (m, 1H) 2.88-2.99 (m, 2H) 3.00-3.11 (m, 1H) 3.29 (s, 2H) 3.42-3.66 (m, 2H) 4.75 (s, 1H) 4.85-4.94 (m, 1H) 4.96-4.98 (m, 1H) 4.98-5.06 (m, 1H) 6.25 (broad s, 1H) 6.55 (d, J=5.32 Hz, 2H) MS (ESI) m/z 384 [M+H$^+$].

Synthesis of Keto-lactone Intermediate (4):

A 3-necked 250-mL RB-flask equipped with a magnetic stirrer, hydrogen inlet, nitrogen inlet and a vacuum adapter was placed under a nitrogen atmosphere and then charged with 5% palladium on carbon (500 mg). The reactor was then charged with a solution of the butenolide intermediate 3 (~1.5 g, 3.9 mmol) in 3:1 v/v ethanol/tetrahydrofuran (100 mL). The reaction vessel was vacuum purged and back-filled with nitrogen three times. The vessel was then vacuum purged and back-filled with hydrogen (1 atm) three times. The reaction was then stirred vigorously for 96 hours under a hydrogen atmosphere (balloon pressure) at which time the hydrogen source was removed and the reaction vessel was placed under a nitrogen atmosphere. The reaction contents were then filtered through a short pad of Celite and the filter cake was washed briefly with dichloromethane. The filtrate was concentrated to dryness using a rotary evaporator to provide 512 mg (35% yield) of crude product. The crude $^1$H NMR spectrum obtained in d4-methanol was qualitatively consistent with the assigned structure, observed as a mixture of two diastereomers. The loss of a broad singlet at 6.25 ppm, corresponding to the α-methine of the butenolide starting material, was a diagnostic NMR signature used to monitor the progress of the reaction. MS (ESI) m/z 386 [M+H$^+$].

Synthesis of Lactone (5):

A 40-mL scintillation vial equipped with a magnetic stirrer was placed under a nitrogen atmosphere and then charged with a solution of the keto-lactone 4 (500 mg, 1.3 mmol) dissolved in acetic acid (6.0 mL). The reaction mixture was cooled to 10° C. and then sodium triacetoxyborohydride (820 mg, 3.9 mmol) was added as a solid in four equal portions. The reaction was stirred vigorously at 10° C. for 90 minutes. Acetone (6.0 mL) was then added and the cooling bath was removed. Stirring was continued for an additional two hours during which time the mixture was allowed to equilibrate to room temperature. The solvent was removed in vacuo and the resulting residue was partitioned between ethyl acetate (30 mL) and water (30 mL). Solid sodium carbonate was then added to the vigorously stirring biphasic mixture until a pH of 9 to 10 was observed. The layers were then separated and the aqueous phase was extracted with additional ethyl acetate (3×30 mL). The combined organic extracts were washed with saturated aqueous sodium chloride, dried over sodium sulfate and concentrated to a crude residue using a rotary evaporator. The resulting residue was purified by normal phase chromatography using a 120-gram Isco Gold RediSep R$_f$ silica gel column. The column was eluted with dichloromethane (A) and a 95:5 v/v solution of dichloromethane/methanol (B) with a 0-60% gradient over 30 minutes and held at 60% B for 10 additional minutes to afford lactone 5 (182 mg, 35% yield) as a white powder after freeze-drying from aqueous acetonitrile. $^1$H NMR (400 MHz, METHANOL-d4) δ ppm 1.00-1.16 (m, 1H) 1.38-1.56 (m, 2H) 1.61 (d, J=2.83 Hz, 2H) 2.19-2.30 (m, 1H) 2.30-2.43 (m, 2H) 2.49-2.75 (m, 5H) 2.78-2.96 (m, 2H) 3.04-3.17 (m, 1H) 4.11-4.20 (m, 2H)

4.40-4.51 (m, 1H) 4.53 (d, J=4.34 Hz, 1H) 6.51 (d, J=8.05 Hz, 1H) 6.63 (d, J=8.10 Hz, 1H) MS (ESI) m/z 388 [M+H$^+$].

Synthesis of Compound 1:

A 40-mL scintillation vial equipped with a magnetic stirrer was charged with lactone 5 (150 mg, 0.39 mmol) followed by tetrahydrofuran (4.0 mL). To the stirring mixture was added 1M aqueous lithium hydroxide (1.16 mL, 1.2 mmol) and the reaction was stirred at room temperature for 4 hours. The volatile organics were then removed in vacuo and the resulting aqueous solution was diluted with additional water (2 mL). A 0.2M acetic acid/potassium acetate aqueous buffer was then added until a pH of 5-6 was obtained and the resulting aqueous solution was transferred to a loading cartridge that was pre-packed with Celite. The cartridge containing adsorbed aqueous Compound 1 was then affixed to a 100-gram Isco Gold RediSep R$_f$ C18 column. The column was eluted with 10 mM aqueous ammonium acetate (A) and 10 mM ammonium acetate in methanol (B) with a 0-45% gradient over 22 minutes and held at 45% B for 5 additional minutes to afford Compound 1 (179 mg) as a dark semi-solid, contaminated with residual ammonium acetate. This material was then re-dissolved in a minimal volume of water and freeze-dried repeatedly. The lyophilization process was periodically assayed by $^1$H NMR and continued until the acetate resonance (s, 1.90 ppm) was integrated to give a value that was <0.25, relative to an Compound 1 proton. The lyophilization required approximately 7 days in total in order to meet this specification. The exhaustively lyophilized Compound 1 was observed as a free-flowing off-white solid and was obtained as a mixture of two diastereomers. A small sample of the mixture was resolved using an Isco Gold RediSep R$_f$C18 column in order to obtain analytical samples of the individual diastereomers. First-eluting Compound 1 diastereomer: $^1$H NMR (400 MHz, METHANOL-d4) δ ppm 1.12-1.28 (m, 1H) 1.54-1.80 (m, 4H) 2.09-2.23 (m, 1H) 2.24-2.34 (m, 1H) 2.35-2.46 (m, 1H) 2.50-2.65 (m, 1H) 2.74-2.91 (m, 1H) 2.95-3.17 (m, 2H) 3.20-3.30 (m, 3H) 3.40-3.50 (m, 1H) 3.53-3.64 (m, 1H) 3.67-3.80 (m, 1H) 4.15-4.31 (m, 1H) 4.56-4.69 (m, 1H) 6.55-6.66 (m, 1H) 6.67-6.78 (m, 1H) MS (ESI) m/z 406 [M+H$^+$]. Second-eluting Compound 1 diastereomer: $^1$H NMR (400 MHz, METHANOL-d4) δ ppm 1.12-1.28 (m, 1H) 1.48-1.79 (m, 4H) 2.13-2.26 (m, 1H) 2.29-2.43 (m, 2H) 2.48-2.74 (m, 2H) 2.87-3.01 (m, 2H) 3.07-3.17 (m, 1H) 3.17-3.27 (m, 1H) 3.38-3.50 (m, 2H) 3.55-3.69 (m, 1H) 4.08-4.29 (m, 1H) 4.54-4.68 (m, 1H) 6.54-6.64 (m, 1H) 6.66-6.74 (m, 1H) MS (ESI) m/z 406 [M+H$^+$].

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLE 1

Abuse Liability Receptor Binding Screen:

The binding of nalbuphine and Compound 1 of the present invention and a known nalbuphine metabolite, nalbuphine-3-beta-D-glucuronid (sometimes referred to as M5 in the following studies), to brain receptors associated with abuse potential was assessed in an in vitro binding affinity screen. The abuse liability screen included 44 targets (receptors, transporters, on gated-channel systems) related to the dopamine, norepinephrine, serotonin, gamma-aminobutyric acid (GABA), acetylcholine, N-methyl-D-aspartate (NMDA) cannabinoid and opioid neurotransmitter systems as recommended in FDA Draft guidance on Assessment of Abuse Potential of Drugs, January 2010.

Screening studies were conducted at 10,000 nM for nalbuphine and 25,000 nM for Compound 1 and M5 corresponding to 43-, 1.6-, and 2.4-fold the mean C$_{max}$ concentrations observed at the highest clinical dose tested in subjects that need hemodialysis (HD).

Compound binding was calculated as a % inhibition of the binding of a radioactively labeled ligand specific for each target.

Nalbuphine showed significant binding to μ-, κ-, and δ-opioid receptors (95-100% inhibition). Compound 1 showed affinity to μ-opioid receptor (92%) only, while metabolite M5 had affinity to the μ and κ-opioid receptor (94 and 78%). Neither Compound 1 or M5 bind to the δ-opioid receptors (<16%) (Table 1).

TABLE 1

Opioid receptor binding study

| Cell/Tissue System | [$^3$H] ligand | NAL IC50 (nM) | NAL Ki (nM) | Compound 1 IC50 (nM) | Compound 1 Ki (nM) | M5 IC50 (nM) | M5 Ki (nM) | NAL Selectivity^ relative to Comp1 | NAL Selectivity^ relative to M5 |
|---|---|---|---|---|---|---|---|---|---|
| HEK-μ$^2$ | DAMGO | 3.5 | 1.4 | 3,200 | 1,300 | 1,800 | 750 | 929 | 536 |
| CHO-κ$^1$ | U 69593 | 5.4 | 3.6 | 74,000 | 49,000 | 8,300 | 5,500 | 13,611 | 1,528 |
| CHO-δ$^1$ | DPDPE | 500 | 300 | 11% @ 25,000 nM$^3$ | — | 16% @ 25,000 nM$^3$ | — | NA | NA |

$^1$cloned human opioid receptor expressed in CHO;
$^2$rat opioid receptor expressed in HEK cells;
$^3$[$^3$H]DADLE;
^Compound 1 or M5 Ki/NAL Ki @ μ-or k-receptor
Opioid agonist radioligand: DAMGO: ([D-Ala2, N-MePhe4, Gly-ol]-enkephalin) & DPDPE: D-Penicillamine(2, 5)-enkephalin Except for binding to the opioid receptors, nalbuphine, its known metabolite M5, and Compound 1 showed weak to no affinity (<34% inhibition) to all the other non-opioid receptors (Table 2).

Results showing an inhibition or stimulation higher than 50% are considered to represent significant effects of the test compounds.

TABLE 2

| Compound | Test Concentration | % Inhibition of Control Specific Binding | | |
|---|---|---|---|---|
| | | $1^{st}$ | $2^{nd}$ | Mean |
| $\alpha_{1A}$ (h) (antagonist radioligand) | | | | |
| Nalbuphine | 1.0E−05M | 0.0 | −11.0 | −5.5 |
| M5 | 2.5E−05M | −0.1 | 3.4 | 1.6 |
| Compound 1 | 2.5E−05M | 1.6 | 0.0 | 0.8 |
| $\alpha_{2A}$ (h) (antagonist radioligand) | | | | |
| Nalbuphine | 1.0E−05M | −2.1 | −2.8 | −2.5 |
| M5 | 2.5E−05M | −0.5 | −5.7 | −3.1 |
| Compound 1 | 2.5E−05M | −0.2 | −11.1 | −5.7 |
| $\alpha_{2B}$ (h) (antagonist radioligand) | | | | |
| Nalbuphine | 1.0E−05M | −3.8 | 5.5 | 0.8 |
| M5 | 2.5E−05M | 15.3 | 2.1 | 8.7 |
| Compound 1 | 2.5E−05M | 6.1 | −1.0 | 2.5 |
| $\alpha_{2C}$ (h) (antagonist radioligand) | | | | |
| Nalbuphine | 1.0E−05M | 15.3 | 16.8 | 16.1 |
| M5 | 2.5E−05M | 12.1 | 6.5 | 9.3 |
| Compound 1 | 2.5E−05M | −4.9 | 2.5 | −1.2 |
| $\beta_1$ (h) (agonist radioligand) | | | | |
| Nalbuphine | 1.0E−05M | −9.8 | −13.1 | −11.4 |
| M5 | 2.5E−05M | −5.4 | 4.8 | −0.3 |
| Compound 1 | 2.5E−05M | −3.8 | −8.4 | −6.1 |
| $\beta_2$ (h) (agonist radioligand) | | | | |
| Nalbuphine | 1.0E−05M | 6.8 | −6.3 | 0.3 |
| M5 | 2.5E−05M | −4.6 | 15.3 | 5.4 |
| Compound 1 | 2.5E−05M | 3.3 | 16.1 | 9.7 |
| BZD (central) (agonist radioligand) | | | | |
| Nalbuphine | 1.0E−05M | −16.7 | 3.4 | −6.7 |
| M5 | 2.5E−05M | −13.2 | 2.1 | −5.6 |
| Compound 1 | 2.5E−05M | 3.4 | 3.0 | 3.2 |
| $CB_1$ (h) (agonist radioligand) | | | | |
| Nalbuphine | 1.0E−05M | −8.7 | −5.1 | −6.9 |
| M5 | 2.5E−05M | −2.9 | 12.9 | 5.0 |
| Compound 1 | 2.5E−05M | 17.0 | 13.5 | 15.3 |
| $CB_2$ (h) (agonist radioligand) | | | | |
| Nalbuphine | 1.0E−05M | 2.0 | 13.6 | 7.8 |
| M5 | 2.5E−05M | −13.1 | −23.1 | −18.1 |
| Compound 1 | 2.5E−05M | −14.6 | −11.0 | −12.8 |
| $D_1$ (h) (antagonist radioligand) | | | | |
| Nalbuphine | 1.0E−05M | −9.0 | −4.0 | −6.5 |
| M5 | 2.5E−05M | −12.1 | 2.2 | −5.0 |
| Compound 1 | 2.5E−05M | −17.0 | 6.7 | −5.2 |
| $D_{2S}$ (h) (antagonist radioligand) | | | | |
| Nalbuphine | 1.0E−05M | 14.8 | 12.4 | 13.6 |
| M5 | 2.5E−05M | −1.6 | 7.2 | 2.8 |
| Compound 1 | 2.5E−05M | 18.8 | 8.3 | 13.6 |
| $GABA_{A1}$ (h) ($\alpha1, \beta2, \gamma2$) (antagonist radioligand) | | | | |
| Nalbuphine | 1.0E−05M | −12.7 | −11.1 | −11.9 |
| M5 | 2.5E−05M | −1.4 | −0.8 | −1.1 |
| Compound 1 | 2.5E−05M | −8.2 | −8.1 | −8.1 |
| AMPA (antagonist radioligand) | | | | |
| Nalbuphine | 1.0E−05M | −1.0 | −8.0 | −4.5 |
| M5 | 2.5E−05M | −8.0 | −11.1 | −9.6 |
| Compound 1 | 2.5E−05M | 0.9 | −3.7 | −1.4 |
| kainate (agonist radioligand) | | | | |
| Nalbuphine | 1.0E−05M | −11.0 | −37.0 | −24.0 |
| M5 | 2.5E−05M | 36.7 | 32.2 | 34.4 |
| Compound 1 | 2.5E−05M | 6.3 | 34.1 | 20.2 |
| NMDA (antagonist radioligand) | | | | |
| Nalbuphine | 1.0E−05M | −4.2 | −13.4 | −8.8 |
| M5 | 2.5E−05M | −15.9 | −14.7 | −15.3 |
| Compound 1 | 2.5E−05M | −12.5 | −9.8 | −11.1 |
| glycine (strychnine-insensitive) (antagonist radioligand) | | | | |
| Nalbuphine | 1.0E−05M | −9.7 | −9.9 | −9.8 |
| M5 | 2.5E−05M | −7.7 | −8.6 | −8.1 |
| Compound 1 | 2.5E−05M | −13.5 | −9.7 | −11.6 |
| $M_1$ (h) (antagonist radioligand) | | | | |
| Nalbuphine | 1.0E−05M | −2.1 | 0.3 | −0.9 |
| M5 | 2.5E−05M | 1.5 | 9.3 | 5.4 |
| Compound 1 | 2.5E−05M | −8.0 | 7.8 | −0.1 |
| $M_2$ (h) (antagonist radioligand) | | | | |
| Nalbuphine | 1.0E−05M | −10.4 | 2.4 | −4.0 |
| M5 | 2.5E−05M | −11.1 | 7.6 | −1.8 |
| Compound 1 | 2.5E−05M | −7.9 | 5.4 | −1.3 |
| $M_3$ (h) (antagonist radioligand) | | | | |
| Nalbuphine | 1.0E−05M | −8.6 | 0.8 | −3.9 |
| M5 | 2.5E−05M | 2.8 | 6.6 | 4.7 |
| Compound 1 | 2.5E−05M | 10.6 | 13.6 | 12.1 |
| $M_4$ (h) (antagonist radioligand) | | | | |
| Nalbuphine | 1.0E−05M | −24.9 | −2.7 | −13.8 |
| M5 | 2.5E−05M | −7.9 | 16.6 | 4.4 |
| Compound 1 | 2.5E−05M | 11.4 | 20.6 | 16.0 |
| $M_5$ (h) (antagonist radioligand) | | | | |
| Nalbuphine | 1.0E−05M | −13.2 | 6.7 | −3.2 |
| M5 | 2.5E−05M | 9.9 | 0.7 | 5.3 |
| Compound 1 | 2.5E−05M | 0.6 | 3.9 | 2.3 |
| N neuronal $\alpha4\beta2$ (h) (agonist radioligand) | | | | |
| Nalbuphine | 1.0E−05M | −6.5 | −4.6 | −5.5 |
| M5 | 2.5E−05M | 0.8 | −2.0 | −0.6 |
| Compound 1 | 2.5E−05M | −4.1 | −1.5 | −2.8 |
| N neuronal $\alpha7$ (h) (antagonist radioligand) | | | | |
| Nalbuphine | 1.0E−05M | 9.9 | 13.9 | 11.9 |
| M5 | 2.5E−05M | −6.0 | −0.4 | −3.2 |
| Compound 1 | 2.5E−05M | −3.2 | 4.6 | 0.7 |
| $\delta_2$ (h) (agonist radioligand) | | | | |
| Nalbuphine | 1.0E−05M | 93.7 | 96.6 | 95.2 |
| M5 | 2.5E−05M | 13.9 | 18.2 | 16.0 |
| Compound 1 | 2.5E−05M | 8.5 | 13.5 | 11.0 |
| $\kappa$ (KOP) (agonist radioligand) | | | | |
| Nalbuphine | 1.0E−05M | 99.9 | 100.3 | 100.1 |
| M5 | 2.5E−05M | 77.4 | 77.6 | 77.5 |
| Compound 1 | 2.5E−05M | 16.1 | 35.2 | 25.7 |
| $\mu$ (MOP) (h) (agonist radioligand) | | | | |
| Nalbuphine | 1.0E−05M | 99.9 | 108.0 | 103.9 |
| M5 | 2.5E−05M | 94.2 | 94.0 | 94.1 |
| Compound 1 | 2.5E−05M | 90.1 | 94.0 | 92.0 |
| $OX_1$ (h) (agonist radioligand) | | | | |
| Nalbuphine | 1.0E−05M | −1.1 | −4.1 | −2.6 |
| M5 | 2.5E−05M | 5.5 | −1.5 | 2.0 |
| Compound 1 | 2.5E−05M | 5.3 | −5.9 | −0.3 |
| $OX_2$ (h) (agonist radioligand) | | | | |
| Nalbuphine | 1.0E−05M | −11.3 | −7.4 | −9.4 |
| M5 | 2.5E−05M | −3.5 | −2.4 | −2.9 |
| Compound 1 | 2.5E−05M | −9.6 | −11.9 | −10.7 |

TABLE 2-continued

| Compound | Test Concentration | % Inhibition of Control Specific Binding | | |
|---|---|---|---|---|
| | | 1st | 2nd | Mean |
| PCP (antagonist radioligand) | | | | |
| Nalbuphine | 1.0E−05M | −4.3 | 12.0 | 3.9 |
| M5 | 2.5E−05M | −1.1 | 4.9 | 1.9 |
| Compound 1 | 2.5E−05M | −12.2 | −1.4 | −6.8 |
| 5-HT$_{1A}$ (h) (agonist radioligand) | | | | |
| Nalbuphine | 1.0E−05M | −8.8 | −1.8 | −5.3 |
| M5 | 2.5E−05M | −7.0 | 3.4 | −1.8 |
| Compound 1 | 2.5E−05M | −5.6 | 3.5 | −1.0 |
| 5-HT$_{2A}$ (h) (agonist radioligand) | | | | |
| Nalbuphine | 1.0E−05M | −7.5 | 3.2 | −2.1 |
| M5 | 2.5E−05M | −4.4 | 6.5 | 1.1 |
| Compound 1 | 2.5E−05M | −2.5 | −4.8 | −3.7 |
| 5-HT$_{2B}$ (h) (agonist radioligand) | | | | |
| Nalbuphine | 1.0E−05M | −11.7 | −8.9 | −10.3 |
| M5 | 2.5E−05M | −3.4 | 3.9 | 0.2 |
| Compound 1 | 2.5E−05M | −15.6 | −6.1 | −10.8 |
| 5-HT$_{2C}$ (h) (agonist radioligand) | | | | |
| Nalbuphine | 1.0E−05M | 1.7 | 0.4 | 1.1 |
| M5 | 2.5E−05M | −7.9 | −8.2 | −8.0 |
| Compound 1 | 2.5E−05M | −11.6 | −6.6 | −9.1 |
| 5-HT$_3$ (h) (antagonist radioligand) | | | | |
| Nalbuphine | 1.0E−05M | 2.7 | 20.7 | 11.7 |
| M5 | 2.5E−05M | 3.2 | 10.9 | 7.0 |
| Compound 1 | 2.5E−05M | 2.9 | 6.2 | 4.6 |
| GR (h) (agonist radioligand) | | | | |
| Nalbuphine | 1.0E−05M | 1.2 | −10.5 | −4.7 |
| M5 | 2.5E−05M | 0.8 | −5.4 | −2.3 |
| Compound 1 | 2.5E−05M | −0.5 | −21.5 | −11.0 |
| ER (non-selective) (h) (agonist radioligand) | | | | |
| Nalbuphine | 1.0E−05M | 0.5 | −1.8 | −0.6 |
| M5 | 2.5E−05M | 9.0 | 10.6 | 9.8 |
| Compound 1 | 2.5E−05M | −8.0 | 4.3 | −1.9 |
| AR (h) (agonist radioligand) | | | | |
| Nalbuphine | 1.0E−05M | −1.2 | −1.3 | −1.2 |
| M5 | 2.5E−05M | 4.9 | −0.8 | 2.1 |
| Compound 1 | 2.5E−05M | −7.1 | −0.4 | −3.8 |
| Ca$^{2+}$ channel (N) (antagonist radioligand) | | | | |
| Nalbuphine | 1.0E−05M | 7.1 | 3.9 | 5.5 |
| M5 | 2.5E−05M | −10.9 | 2.5 | −4.2 |
| Compound 1 | 2.5E−05M | −11.7 | −3.8 | −7.7 |
| Na$^+$ channel (site 2) (antagonist radioligand) | | | | |
| Nalbuphine | 1.0E−05M | 3.2 | 6.9 | 5.1 |
| M5 | 2.5E−05M | −2.1 | 24.8 | 11.4 |
| Compound 1 | 2.5E−05M | −4.4 | 21.0 | 8.3 |
| Cl$^−$ channel (GABA-gated) (antagonist radioligand) | | | | |
| Nalbuphine | 1.0E−05M | −15.7 | −4.6 | −10.2 |
| M5 | 2.5E−05M | 3.3 | −7.4 | −2.1 |
| Compound 1 | 2.5E−05M | 1.7 | 1.0 | 1.3 |
| Norepinephrine transporter (h) (antagonist radioligand) | | | | |
| Nalbuphine | 1.0E−05M | −0.4 | 2.3 | 0.9 |
| M5 | 2.5E−05M | −11.4 | 3.2 | −4.1 |
| Compound 1 | 2.5E−05M | −18.2 | 8.1 | −5.1 |
| Dopamine transporter (h) (antagonist radioligand) | | | | |
| Nalbuphine | 1.0E−05M | 3.1 | 10.0 | 6.6 |
| M5 | 2.5E−05M | −2.0 | 12.1 | 5.1 |
| Compound 1 | 2.5E−05M | 0.0 | 10.6 | 5.3 |
| GABA transporter (antagonist radioligand) | | | | |
| Nalbuphine | 1.0E−05M | 0.9 | −3.0 | −1.1 |
| M5 | 2.5E−05M | 0.9 | −2.8 | −1.0 |
| Compound 1 | 2.5E−05M | 7.4 | −6.2 | 0.6 |
| 5-HT transporter (h) (antagonist radioligand) | | | | |
| Nalbuphine | 1.0E−05M | −17.0 | −6.0 | −11.5 |
| M5 | 2.5E−05M | −12.2 | 4.5 | −3.9 |
| Compound 1 | 2.5E−05M | −11.9 | 1.9 | −5.0 |

IC$_{50}$ Determination

TABLE 3

Determination of IC$_{50}$ of nalbuphine against a δ-opioid receptor agonist ligand

| Compound I.D. | IC50 (M) | Ki (M) | nH | Test Conc. | % Inhibition of Control Specific Binding | | | Flags | |
|---|---|---|---|---|---|---|---|---|---|
| | | | | | 1st | 2nd | Mean | 1st | 2nd |
| δ2 (DOP) (h) (agonist radioligand) | | | | | | | | | |
| Nalbuphine | 5.0E−07M | 3.0E−07M | 0.8 | 1.0E−09M | 8.6 | 1.3 | 5.0 | | |
| | | | | 1.0E−08M | 16.8 | 10.8 | 13.8 | | |
| | | | | 3.0E−08M | 16.5 | 18.3 | 17.4 | | |
| | | | | 1.0E−07M | 25.9 | 30.2 | 28.0 | | |
| | | | | 3.0E−07M | 50.4 | 38.0 | 44.2 | | |
| | | | | 1.0E−06M | 64.5 | 69.1 | 66.8 | | |
| | | | | 3.0E−06M | 82.9 | 88.1 | 85.5 | | |
| | | | | 3.0E−05M | 97.5 | 99.0 | 98.3 | | |

TABLE 4

Determination of $IC_{50}$ of test compounds against a κ-opioid receptor agonist ligand

| Compound I.D. k (KOP) (agonist radioligand) | IC50 (M) | Ki (M) | nH | Test Conc. | % Inhibition of Control Specific Binding | | | Flags | |
|---|---|---|---|---|---|---|---|---|---|
| | | | | | $1^{st}$ | $2^{nd}$ | Mean | $1^{st}$ | $2^{nd}$ |
| Nalbuphine | 5.4E−09M | 3.6E−09M | 0.8 | 3.0E−10M | 2.3 | −3.4 | −0.5 | | |
| | | | | 3.0E−09M | 33.4 | 58.5 | 46.0 | | |
| | | | | 1.0E−08M | 59.6 | 58.2 | 58.9 | | |
| | | | | 3.0E−08M | 82.6 | 77.3 | 79.9 | | |
| | | | | 1.0E−07M | 91.2 | 93.5 | 92.4 | | |
| | | | | 3.0E−07M | 97.1 | 98.8 | 97.9 | | |
| | | | | 1.0E−06M | 98.6 | 101.4 | 100.0 | | |
| | | | | 1.0E−05M | 99.4 | 101.9 | 100.7 | | |
| Nalbuphine-3-beta-D-glucuronid | 8.3E−06M | 5.5E−06M | 0.8 | 3.0E−08M | −2.6 | 12.0 | 4.7 | | |
| | | | | 1.0E−07M | 8.1 | 10.5 | 9.3 | | |
| | | | | 3.0E−07M | 15.0 | 20.7 | 17.8 | | |
| | | | | 1.0E−06M | 14.6 | 10.0 | 12.3 | | |
| | | | | 3.0E−06M | 29.5 | 41.9 | 35.7 | | |
| | | | | 1.0E−05M | 55.6 | 63.7 | 59.6 | | |
| | | | | 3.0E−05M | 74.8 | 73.7 | 74.2 | | |
| | | | | 1.0E−04M | 87.5 | 87.6 | 87.5 | | |
| Compound 1 | 7.4E−05M | 4.9E−05M | 0.7 | 3.0E−08M | 5.5 | −0.1 | 2.7 | | |
| | | | | 1.0E−07M | 4.1 | −2.2 | 1.0 | | |
| | | | | 3.0E−07M | 16.1 | 1.6 | 8.9 | | |
| | | | | 1.0E−06M | 34.5 | 40.4 | 37.5 | { }, OUTLIER | { }, OUTLIER |
| | | | | 3.0E−06M | 5.7 | 11.5 | 8.6 | | |
| | | | | 1.0E−05M | 11.7 | 23.9 | 17.8 | | |
| | | | | 3.0E−05M | 36.8 | 42.8 | 39.8 | | |
| | | | | 1.0E−04M | 55.9 | 53.9 | 54.9 | | |

{ }: That replicate was excluded from the calculation
OUTLIER: Data is outside of the expected range of values for the data set and was excluded from calculation.

TABLE 5

Determination of $IC_{50}$ of test compounds against a μ-opioid receptor agonist ligand

| Compound I.D. μ (KOP) (h) (agonist radioligand) | IC50 (M) | Ki (M) | nH | Test Conc. | % Inhibition of Control Specific Binding | | | Flags | |
|---|---|---|---|---|---|---|---|---|---|
| | | | | | $1^{st}$ | $2^{nd}$ | Mean | $1^{st}$ | $2^{nd}$ |
| Nalbuphine | 3.5E−09M | 1.4E−09M | 1.4 | 3.0E−10M | −19.4 | −4.2 | −11.8 | | |
| | | | | 3.0E−09M | 41.1 | 50.6 | 45.8 | | |
| | | | | 1.0E−08M | 66.5 | 71.2 | 68.9 | | |
| | | | | 3.0E−08M | 80.5 | 88.1 | 84.3 | | |
| | | | | 1.0E−07M | 84.5 | 97.1 | 90.8 | | |
| | | | | 3.0E−07M | 85.5 | 95.0 | 90.2 | | |
| | | | | 1.0E−06M | 90.0 | 96.6 | 93.3 | | |
| | | | | 1.0E−05M | 86.9 | 96.6 | 91.8 | | |
| Nalbuphine-3-beta-D-glucuronid | 1.8E−06M | 7.5E−07M | 0.7 | 3.0E−09M | −17.7 | −4.2 | −11.0 | | |
| | | | | 3.0E−08M | −7.3 | 2.9 | −2.2 | | |
| | | | | 1.0E−07M | 3.1 | 9.1 | 6.1 | | |
| | | | | 3.0E−07M | −4.0 | 18.6 | 7.3 | | |
| | | | | 1.0E−06M | 26.2 | 42.5 | 34.3 | | |
| | | | | 3.0E−06M | 49.6 | 64.1 | 56.9 | | |
| | | | | 1.0E−05M | 71.7 | 75.3 | 73.5 | | |
| | | | | 1.0E−04M | 88.6 | 91.4 | 90.0 | | |
| Compound 1 | 3.2E−06M | 1.3E−06M | 0.6 | 3.0E−09M | −23.4 | −13.5 | −18.4 | | |
| | | | | 3.0E−08M | −7.1 | 11.2 | 2.1 | | |
| | | | | 1.0E−07M | −6.6 | 5.3 | −0.7 | | |
| | | | | 3.0E−07M | −6.8 | 12.2 | 2.7 | | |
| | | | | 1.0E−06M | 7.9 | 35.4 | 21.6 | | |
| | | | | 3.0E−06M | 36.1 | 55.6 | 45.8 | | |
| | | | | 1.0E−05M | 55.6 | 68.9 | 62.2 | | |
| | | | | 1.0E−04M | 82.9 | 94.2 | 88.6 | | |

Opioid Receptor Interaction Studies:

In addition, in vitro binding and functional opioid receptor interaction studies were conducted to characterize side-by-side nalbuphine, its known metabolite M5, and Compound 1 in the cloned mouse μ-opioid receptors expressed in human embryonic kidney (HEK) cell lines and cloned human δ- and κ-opioid receptors expressed in Chinese Hamster Ovary (CHO) cells.

000 nM, 60%) and κ-agonist (EC50=13,000 nM, 74%) at concentrations 3-fold and 1.3-fold higher, respectively, than its $C_{max}$ value in HD patients (10,400 nM) (Table 6).

In conclusion, nalbuphine is a κ-agonist and a partial μ-agonist/antagonist with high binding affinity to the κ- and μ-receptors and a weak δ-partial agonist. Both Compound 1 and M5 have low binding and weak μ- and/or κ-partial agonists at concentrations exceeding their plasma $C_{max}$.

TABLE 6

Opioid cell functional assay conducted

| Cell/Tissue System | [$^3$H] Ligand | Nalbuphine EC50 (nM) | Nalbuphine Max Inh (%) | Compound 1 EC50 (nM) | Compound 1 Max Inh (%) | M5 EC50 (nM) | M5 Max Inh (%) |
|---|---|---|---|---|---|---|---|
| Opioid-agonist assay | | | | | | | |
| HEK-μ$^2$ | [$^3$H]DAMGO | 4.1 | 71% | 78,000 | 61% | 33,000 | ~60% |
| CHO-κ$^1$ | [$^3$H]U 69593 | 7.9 | 92% | >100,000 | 14% | 13,000 | 74% |
| CHO-δ$^1$ | [$^3$H] DPDPE | >10,000 | 28% | ND | ND | ND | ND |
| Opioid-antagonist assay | | | | | | | |
| HEK-μ$^2$ | CTOP | NC | 24% @ 30,000 nM | NC | −1% @ 30,000 nM | NC | 16% @ 300,000 nM |
| CHO-κ$^1$ | Nor-BNI | NC | −20% @ 30,000 nM | NC | −10% @ 100,000M | NC | −2.8% @ 300,000 nM |
| CHO-δ$^1$ | Natroindole | NC-AGO* | 68% @ 10,000 nM | ND | ND | ND | ND |

$^1$cloned human opioid receptor expressed in CHO;
$^2$rat mouse opioid receptor expressed in HEK cells;
ND: Not determined;
NC: IC50 could not be calculated as inhibition < 25% at highest tested concentration;
NC-AGO (Agonist): IC50 could not be calculated as analyte exhibited agonist-like properties resulting in an apparent inhibition;
CTOP: Somatostatin analogue;
DAMGO: ([D-Ala2, N-MePhe4, Gly-ol]-enkephalin);
DPDPE: D-Penicillamine(2,5)-enkephalin;
Nor-BNI Norbinaltorphimine.

Nalbuphine demonstrated selectivity for the μ- and κ-opioid receptor subtypes relative to the δ-opioid receptor subtypes (Table 1). Binding affinity (Ki) to the opioid receptors in these isolated cell systems showed a nearly 100 to 200-fold higher selectivity to the μ- and κ-opioid relative to the δ-opioid receptor. Affinity to the μ-opioid receptor was 2.6-fold higher than the κ-opioid.

In the cell functional assays, nalbuphine was a full kappa agonist ($IC_{50}$=8 nM) reaching >90% at 300 nM (near plasma $C_{max}$ in HD subjects), a partial μ-agonist/antagonist ($IC_{50}$=4 nM) with a maximal inhibition of 71%, and a weak delta partial agonist (28% at 10,000 nM about 42-fold higher than $C_{max}$). Nalbuphine did not antagonize any of the opioid receptors up to concentrations of 30,000 nM.

The Compound 1 and known nalbuphine metabolite M5 exhibited significantly lower binding affinity to the opioid receptors relative to nalbuphine (about 5 to 13,611-fold lower) (Table 1). In the cell functional assays, both Compound 1 and M5 were weak μ- and/or κ-partial agonists (ranging between 1,600 to 19,000 fold lower than nalbuphine) with no activity at the delta receptor. Compound 1 is a partial μ-agonist ($EC_{50}$=78,000 nM, 61%) at concentrations exceeding the $C_{max}$ in HD patients (~16,000 nM) by nearly 4 folds. M5 is also a weak partial μ-agonist ($EC_{50}$=33, All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A compound having structural formula (I),

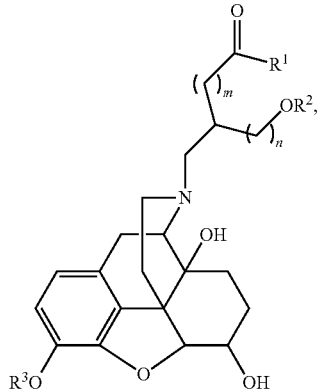

or a salt, solvate, or ester thereof, wherein
R$^1$ is alkyl, OR$^4$, or NR$^5$R$^6$;
R$^2$ is H or alkyl; or alternatively, R$^1$ and OR$^2$, together with the atoms to which they are attached, form a lactone ring;
m is 0 or 1;
n is 1 or 2; and
R$^3$, R$^4$, R$^5$ and R$^6$ are independently hydrogen or alkyl.

2. The compound of claim 1, having structural formula (II),

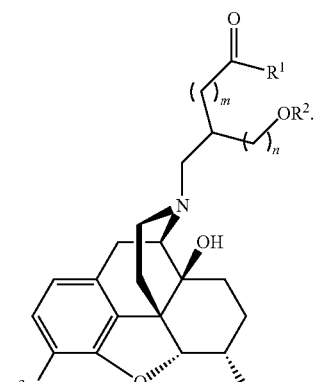

3. The compound of claim 1, wherein R$^1$ is OH, R$^2$ is H, and R$^3$ is H.

4. The compound of claim 1, wherein R$^1$ and OR$^2$, together with the atoms to which they are attached, form a lactone ring.

5. The compound of claim 1, wherein m is 1, and n is 1.

6. The compound of claim 1, wherein m is 1, n is 1, R$^1$ is OH, R$^2$ is H, and R$^3$ is H.

7. The compound of claim 1, wherein m is 1, n is 1, and R$^1$ and OR$^2$, together with the atoms to which they are attached, form a lactone ring.

8. The compound of claim 1, selected from the group consisting of

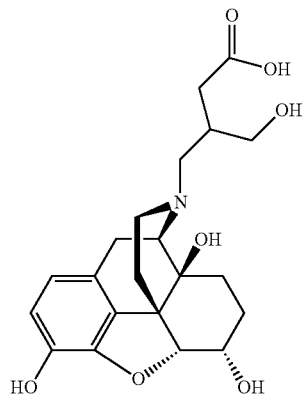 and

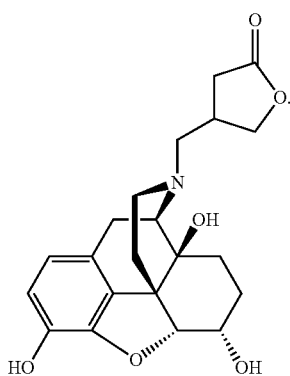

9. The compound of claim 1, wherein the compound is isolated.

10. The compound of claim 9, wherein the compound has a purity of at least about 75%.

11. The compound of claim 9, wherein the compound has a purity of at least about 90%.

12. A pharmaceutical composition comprising the compound of claim 1, or a salt, solvate, or ester thereof, and a pharmaceutically acceptable excipient.

13. The pharmaceutical composition of claim 9, wherein the compound is selected from the group consisting of:

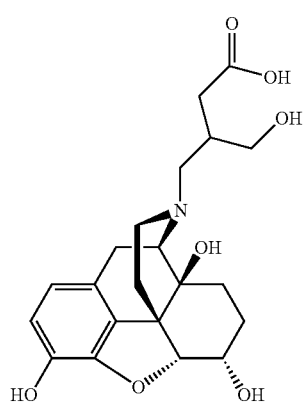 and

-continued

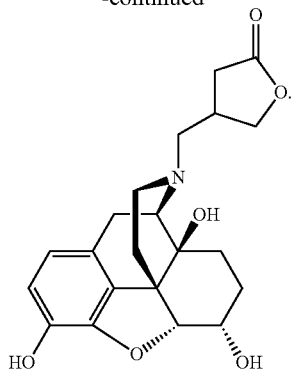

14. The pharmaceutical composition of claim 12, wherein the compound, or a salt, solvate, or ester thereof, is present in an amount of about 0.1% w/w to about 10% w/w.

15. The pharmaceutical composition of claim 14, wherein the compound, or a salt, solvate, or ester thereof, is present in an amount of about 1% w/w to about 10% w/w.

16. A unit dosage form comprising the compound of claim 1, or a salt, solvate or ester thereof, and a pharmaceutically acceptable excipient.

17. The unit dosage form of claim 16, wherein the dosage form is an extended release dosage form.

18. The unit dosage form of claim 16, wherein the compound, or a salt, solvate, or ester thereof, is present in an amount of about 0.1% w/w to about 10% w/w.

19. The unit dosage form of claim 18, wherein the compound, or a salt, solvate, or ester thereof, is present in an amount of about 1% w/w to about 10% w/w.

20. A method of treating a pruritic condition comprising administering a composition comprising an effective amount of the compound of claim 1, or a salt, solvate, or ester thereof, to a subject in need thereof.

21. The method of claim 20, wherein the composition comprises about 0.1% w/w to about 10% w/w of the compound or a salt, solvate, or ester thereof.

22. The pharmaceutical composition of claim 14, wherein the composition is a topical composition.

23. The method of claim 20, wherein the composition is administered topically.

24. A method of treating a gastrointestinal condition in a subject in need thereof, comprising administering a composition comprising an effective amount of the compound of claim 1, or a salt, solvate, or ester thereof.

25. The method of claim 24, wherein the gastrointestinal condition is selected from the group consisting of diarrhea, gastroenteritis, inflammatory bowel disease and short bowel syndrome.

26. The method of claim 24, wherein the composition is delivered topically to the gastrointestinal tract.

* * * * *